US008007526B2

(12) United States Patent
Bezwada

(10) Patent No.: US 8,007,526 B2
(45) Date of Patent: Aug. 30, 2011

(54) DIFUNCTIONALIZED AROMATIC COMPOUNDS AND POLYMERS THEREFROM

(75) Inventor: Rao S Bezwada, Hillsborough, NJ (US)

(73) Assignee: Bezwada Biomedical, LLC, Hillsborough, NJ (US)

( * ) Notice: Subject to any disclaimer, the term of this patent is extended or adjusted under 35 U.S.C. 154(b) by 1298 days.

(21) Appl. No.: 11/565,820

(22) Filed: Dec. 1, 2006

(65) Prior Publication Data

US 2007/0129787 A1 Jun. 7, 2007

Related U.S. Application Data

(60) Provisional application No. 60/741,158, filed on Dec. 1, 2005.

(51) Int. Cl.
A61F 2/06 (2006.01)
A61K 9/14 (2006.01)
A61K 9/00 (2006.01)
A61F 13/00 (2006.01)
A61K 8/02 (2006.01)

(52) U.S. Cl. ....... 623/1.15; 424/484; 424/400; 424/422; 424/401

(58) Field of Classification Search .................. None
See application file for complete search history.

(56) References Cited

U.S. PATENT DOCUMENTS

| | | | |
|---|---|---|---|
| 2,386,454 A | 10/1945 | Frosch | |
| 3,025,323 A | 3/1962 | Rose | |
| 3,044,942 A | 7/1962 | Baptist | |
| 3,155,714 A * | 11/1964 | Mills | 560/96 |
| 3,297,033 A | 1/1967 | Schmitt | |
| 3,371,069 A | 2/1968 | Miyamae | |
| 3,531,561 A | 9/1970 | Trehu | |
| 3,636,956 A | 1/1972 | Schneider | |
| 3,773,737 A | 11/1973 | Goodman | |
| 4,052,988 A | 10/1977 | Doddi | |
| 4,130,639 A | 12/1978 | Shalaby | |
| RE30,170 E | 12/1979 | Goodman et al. | |
| 4,226,243 A | 10/1980 | Jamiolkowski | |
| 4,343,931 A | 8/1982 | Barrows | |
| 4,467,065 A * | 8/1984 | Williams et al. | 524/296 |
| 4,532,928 A | 8/1985 | Bezwada | |
| 4,605,730 A | 8/1986 | Shalaby | |
| 4,653,497 A | 3/1987 | Bezwada | |
| 4,689,424 A | 8/1987 | Shalaby | |
| 4,829,099 A * | 5/1989 | Fuller et al. | 606/214 |
| 4,886,870 A | 12/1989 | D'Amore | |
| 4,912,135 A * | 3/1990 | Taguchi et al. | 514/522 |
| 4,938,949 A | 7/1990 | Borch | |
| 5,082,925 A | 1/1992 | Shalaby | |
| 5,099,060 A | 3/1992 | Kohn | |
| 5,188,815 A * | 2/1993 | Coates et al. | 424/9.8 |
| 5,198,507 A | 3/1993 | Kohn et al. | |
| 5,241,102 A * | 8/1993 | Syoshi et al. | 560/35 |
| 5,264,540 A | 11/1993 | Cooper | |
| 5,321,113 A * | 6/1994 | Cooper et al. | 528/176 |
| 5,587,507 A | 12/1996 | Kohn et al. | |
| 5,594,076 A * | 1/1997 | Gordon et al. | 525/444 |
| 5,658,995 A | 8/1997 | Kohn | |
| 5,759,830 A | 6/1998 | Vacanti | |
| 5,895,150 A | 4/1999 | Watabe | |
| 5,902,599 A | 5/1999 | Anseth | |
| 5,902,874 A | 5/1999 | Roby | |
| 5,914,387 A | 6/1999 | Roby | |
| 5,919,893 A | 7/1999 | Roby | |
| 5,942,252 A | 8/1999 | Tice | |
| 5,951,997 A | 9/1999 | Bezwada | |
| 6,048,521 A | 4/2000 | Kohn et al. | |
| 6,083,491 A * | 7/2000 | Mellul et al. | 424/63 |
| 6,103,255 A | 8/2000 | Levene et al. | |
| 6,120,491 A | 9/2000 | Kohn et al. | |
| 6,120,788 A | 9/2000 | Barrows | |
| 6,273,913 B1 * | 8/2001 | Wright et al. | 623/1.42 |
| 6,468,519 B1 | 10/2002 | Uhrich | |
| 6,689,350 B2 | 2/2004 | Uhrich | |
| 6,773,721 B1 | 8/2004 | Wong | |
| 6,852,308 B2 | 2/2005 | Kohn et al. | |
| 6,861,068 B2 | 3/2005 | Ng | |
| 6,869,615 B2 | 3/2005 | Chen | |
| 6,890,561 B1 | 5/2005 | Blatt | |
| 2002/0169275 A1 | 11/2002 | Matsuda | |
| 2003/0216307 A1 | 11/2003 | Kohn | |
| 2003/0232091 A1 | 12/2003 | Shefer | |
| 2004/0117007 A1 | 6/2004 | Whitbourne | |
| 2005/0048121 A1 | 3/2005 | East | |
| 2005/0074493 A1 | 4/2005 | Mehta | |
| 2005/0095300 A1 | 5/2005 | Wynn | |

(Continued)

FOREIGN PATENT DOCUMENTS

WO   WO 97/39738   10/1997

(Continued)

OTHER PUBLICATIONS

Gutowska et al, J. Biomater. Res., 29, 811-21 (1995).
Hoffman, J. Controlled Release, 6, 297-305 (1987).
Mikos et al, Biomaterials, 14, 323-329 (1993).
Schugens et al, J. Biomed. Mater. Res., 30, 449-462 (1996).

(Continued)

*Primary Examiner* — Robert A Wax
*Assistant Examiner* — William Craigo
(74) *Attorney, Agent, or Firm* — Vance Intellectual Property, PC

(57) ABSTRACT

The present invention relates to compounds of formula I, which are difunctionalized aromatic compounds, and polymers formed from the same.

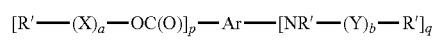

Polymers formed from the di-functionalized aromatics are expected to have controllable degradation profiles, enabling them to release an active component over a desired time range. The polymers are also expected to be useful in a variety of medical applications.

53 Claims, No Drawings

U.S. PATENT DOCUMENTS

| | | |
|---|---|---|
| 2005/0112171 A1 | 5/2005 | Tang |
| 2005/0152958 A1 | 7/2005 | Cordes |
| 2005/0165203 A1 | 7/2005 | Kohn et al. |

FOREIGN PATENT DOCUMENTS

| | | |
|---|---|---|
| WO | WO 98/36013 | 8/1998 |
| WO | WO 99/12990 | 3/1999 |
| WO | WO 99/29885 | 6/1999 |
| WO | WO 01/41753 | 6/2001 |
| WO | WO 02/09767 | 2/2002 |
| WO | WO 02/09768 | 2/2002 |

OTHER PUBLICATIONS

Bulletin of the Material Research Society, Special Issue on Tissue Engineering (Guest Editor: Joachim Kohn), 21 (11), 22-26 (1996).

Remington's Pharmaceutical Sciences, $18^{th}$ ed., Mack Publishing Company, Easton, PA, 1990, p. 1445.

J. Org. Chem, 1959, 24, 523-526.

Helder et al, J. Biomed. Mater. Res., (24), 1005-1020 (1990).

Barrera et al, Macromolecules, (28), 425-432 (1995).

Langer, R., Science 249: 1527-1533 (1990).

\* cited by examiner

DIFUNCTIONALIZED AROMATIC COMPOUNDS AND POLYMERS THEREFROM

CROSS-REFERENCE TO RELATED APPLICATIONS

The present application claims priority benefit under 35 U.S.C. §119(e) of U.S. Provisional Patent Application Ser. No. 60/741,158 filed Dec. 1, 2005. The disclosure this application is incorporated herein by reference.

FIELD OF THE INVENTION

The present invention relates to the discovery of difunctionalized aromatic compounds and polymers derived therefrom, which can have controllable degradation profiles.

BACKGROUND OF THE INVENTION

Polymers prepared from the aromatic compounds, such as terephthalic acid, p-aminobenzoic acid, and p-phenylenediamine exhibit excellent physical properties, but the polymers are not biodegradable. Polyesters derived from terephthalic acid, such as polyethylene terephthalate (PET), polytrimethylene terephthalate (PTT), and poly(1,4-butylene terephthalate) (PBT) are used extensively for making fibers and molding articles. Some of these are polymers that are used in biomedical applications such as non-absorbable surgical sutures, and these polymers are considered to be safe and biocompatible. Unfortunately, these polymers are non-absorbable and, therefore, cannot be used as absorbable sutures or as absorbable polymers for the controlled release of drugs.

Due to the availability and numerous uses of the polymers derived from these aromatic compounds, it is desirable to enhance their value, for example, by functionalizing these aromatic compounds and preparing absorbable polymers therefrom. The resulting absorbable polymers should have a specific controlled degradation profile or range enabling controlled release of drugs over an extended, controllable time range when physically admixed with these polymers.

Synthetic absorbable polymers have been used to produce various surgical products such as sutures, implants, prostheses, and the like, for several years. Illustrative U.S. patents describing such polymers include U.S. Pat. Nos. 3,297,033; 3,044,942; 3,371,069; 3,531,561; 3,636,956; Re. 30,170; and, U.S. Pat. No. 4,052,988.

Implantable surgical devices must be sterile prior to implanting in the body. Sterilization of devices is usually accomplished by the use of heat, ethylene oxide, or gamma radiation using a $^{60}$Co source. In many cases, the use of gamma radiation is the most convenient and most certain way to effect sterilization. However, all of the synthetic absorbable polymers now in commercial use are significantly degraded by gamma radiation. Therefore, unless for some reason degradation of the polymer is desired (for instance, to greatly accelerate the absorption rate), the use of gamma radiation is precluded for the purpose of sterilizing the presently commercial synthetic absorbable polymers.

This invention also provides a new class of polymers that are absorbable and which are expected to be sterilizable by gamma radiation while still retaining a desirable level of physical and biological properties.

SUMMARY OF INVENTION

The present invention provides novel difunctionalized aromatic compounds, which are hydrolysable and can be useful for medical applications (e.g., drug delivery and solvents for dissolving drugs).

The present invention also provides novel, absorbable polymers and co-polymers (e.g., polyesters, polyamides, polyester amides, polyurethanes, and polyanhydrides) derived from the difunctionalized aromatic compounds. These polymers are expected to have controllable degradation profiles.

The present invention also provides novel medical devices comprising difunctionalized aromatic compounds or polymers derived therefrom.

This invention also provides a new class of polymers that are absorbable and that are expected to be sterilizable by gamma radiation while still retaining a desirable level of physical and biological properties.

Other features of the present invention will be pointed out in the following description and claims.

DETAILED DESCRIPTION OF THE PRESENT INVENTION

The present invention provides novel difunctionalized aromatic compounds and absorbable polymers derived from them. The present invention is designed to extend the usefulness of aromatic compounds while retaining their inherent biological properties. The aromatic compounds are functionalized with safe and biocompatible molecules (e.g., glycolic acid, lactic acid, caprolactone, and dioxanone). The novel difunctionalized aromatic compounds of the present invention are expected to have controllable hydrolysis profiles, improved bioavailability, improved efficacy, and enhanced functionality.

Some of the difunctionalized aromatic compounds of the present invention can be monomers from which polymers can be made that are useful for medical applications. For example, an aromatic compound can be functionalized to form functionalized monomers that can then be polymerized to form absorbable polymers (e.g., polyesters, polyamides, polyester amides, polyurethanes, and polyanhydrides). It can be advantageous for the monomers that are to be polymerized to have at least two active sites (e.g., 2 or 3) for polymerization. These active sites include hydroxyl, amino, and carboxylic acid groups (e.g., two hydroxyl groups, a hydroxyl group and a carboxylic acid, a hydroxyl group and an amine group, a carboxylic acid group and an amino group, and two carboxylic acid groups). The difunctionalized aromatic compounds with at least two active sites can also be copolymerized with selected difunctional molecules (e.g., dicarboxylic acids, dialcohols, diisocyanates, amino-alcohols, hydroxy-carboxylic acids, and diamines) based on the starting difunctionalized aromatic to form absorbable polymers. The polymers (and copolymers) of the present invention can also be further reacted/polymerized to form additional useful polymers of the present invention.

The definitions and examples provided in this application are not intended to be limiting, unless specifically stated.

Ar, as used herein, is an aromatic moiety that typically has 1, 2, 3, 4, 5, or 6 aromatic rings (e.g., phenyl) and optionally bear one or more substituents (e.g., 1, 2, 3, 4, 5, or 6) on one of the aromatic rings. Additional examples of the number of aromatic groups present in the aromatic include (a) 1, 2, and 3; (b) 1 and 2; and, (c) 1. Aromatics can be bioactive substances occurring widely in food plants that are eaten regularly by substantial numbers of animals and people and have been found to be safe compounds.

The aromatic rings of the Ar group can be fused together (e.g., naphthyl), bonded together (e.g., bi-phenyl), or linked together via a linking group. Typical linking groups include, O, $S(O)_{0-2}$, NH (or a substituted amine, e.g., $C_{1-6}$ alkyl, phenyl, or benzyl), $C_{1-6}$ alkylene, or a $C_{1-6}$ alkylene wherein one or two of the alkylene carbon atoms is replaced by one or two of the previously noted heteroatoms. The aromatic rings of the Ar group can also be fused to heteroaryl rings and/or non-aromatic rings. Examples of heteroaryl rings include 5-6 membered rings consisting of carbon atoms and 0-4 heteroatoms selected from O, N, and $S(O)_{0-2}$. Examples of non-aromatic rings include 5-6 membered carbocyclic or heterocyclic rings consisting of carbon atoms and 0-3 heteroatoms selected from O, N, and $S(O)_{0-2}$. The non-aromatic rings can consist of 0-2 ring double bonds as well as 0-2 carbonyl groups attached to the ring. Examples of non-aromatic rings include pyran and pyran-one. The non-aromatic rings can also be substituted by 1-2 carbonyl groups, in addition to other substituents defined elsewhere. When more than one aromatic ring is present (e.g., two phenyl rings), then they can be separated by a heteroaryl or non-aromatic ring as described above. For example, a phenyl ring can be bound to a chromene-2-one.

Examples of Ar include the following:

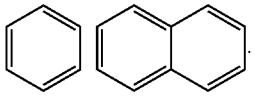

The Ar group of the present invention is substituted or unsubstituted. When substituted, it can be substituted with (a) 1, 2, 3, 4, 5 or 6 R groups; (b) 1, 2, or 3 R groups; (c) 1 or 2 R; or (d) 1 R.

Examples of substituent R include H, =O, O-glycosides, —$(CH_2)_{0-2}$—$OR^a$, —$(CH_2)_{0-2}$—$C_6H_5$, —$(CH_2)_{0-2}$—CHO, Cl, F, Br, I, —$(CH_2)_{0-2}$—OC(O)—$R^a$, —$(CH_2)_{0-2}$—$CO_2$—$R^a$, —$(C(CH_3))_{0-2}$—$CO_2$—$R^a$, —$(CH_2)_{0-2}$—$CO_2$—$(CH_2)_{1-2}$—$CO_2$—$R^a$, —$(C(CH_3))_{0-2}$—$CO_2$—$(CH_2)_{1-2}$—$CO_2$—$R^a$, —$(CH_2)_{0-2}$—CO—$R^a$, —$O(CH_2)_{0-2}$—$C_6H_5$, —$O(CH_2)_{1-2}$—$CO_2$—$R^a$, —$O(C(CH_3))_{1-2}$—$CO_2$—$R^a$, —$O(CH_2)_{1-2}$—CO—$R^a$, —$CO_2(CH_2)_{1-2}$—$CO_2$—$R^a$, —$CO_2(C(CH_3))_{1-2}$—$CO_2$—$R^a$, —$(CH_2)_{0-2}$—$NO_2$, —$(CH_2)_{0-2}$—$NR^aR^a$, —$(CH_2)_{0-2}$—$NR^aCOR^a$, —$(CH_2)_{0-2}$—$NR^aC(O)(CH_2)_{1-2}OR^a$, —$C_6H_5$, —$C_6H_5OR^a$, and —$C_6H_5$—CH=$CHCO_2R^a$.

Examples of $R^a$ include H and $C_{1-6}$ alkyl;

As described herein, the difunctionalized aromatic compounds and polymers of the present invention are expected to be useful in medical applications/medical devices. Medical application/medical devices, as used herein, encompass medical and biomedical applications and include all types of applications involved in the practice of medicine that would benefit from a material that decomposes harmlessly within a known period of time. Examples include medical and surgical devices, which include drug delivery systems (e.g., a site-specific or systemic drug delivery systems or matrices), tissue engineering (e.g., tissue scaffold), stent coatings, stents, porous devices, implantable medical devices, molded articles (e.g., vascular grafts, stents, bone plates, sutures, implantable sensors, and barriers for surgical adhesion prevention), wound closure devices (e.g., surgical clips, staples, and sutures), coatings (e.g., for endoscopic instruments, sutures, stents, and needles), fibers or filaments (which may be attached to surgical needles or fabricated into materials including sutures or ligatures, multifilament yarn, sponges, gauze, tubes, and sheets for typing up and supporting damaged surface abrasions), rods, films (e.g., adhesion prevention barriers), knitted products, foodstuffs, nutritional supplements, nutriceuticals, cosmetics, pharmaceuticals, biodegradable chewing gums, flavors, enhanced drugs, drug intermediates, cancer preventing agents, antioxidants, controlled release preparations, and solvents for drugs. Examples of knitted products, woven or non-woven, and molded products include: burn dressings; hernia patches; medicated dressings; fascial substitutes; gauze, fabric, sheet, felt, or sponge for liver hemostasis; gauze bandages; arterial graft or substitutes; bandages for skin surfaces; suture knot clip; orthopedic pins, clamps, screws, and plates; clips (e.g., for vena cava); staples; hooks, buttons, and snaps; bone substitutes (e.g., mandible prosthesis); intrauterine devices (e.g., spermicidal devices); draining or testing tubes or capillaries; surgical instruments; vascular implants or supports; vertebral discs; extracorporeal tubing for kidney and heart-lung machines; and, artificial skin.

As used herein, "polymer" includes both polymers and copolymers depending on the number of different monomers used.

The present invention provides novel difunctionalized aromatic compounds of formula I or a pharmaceutically acceptable salt thereof:

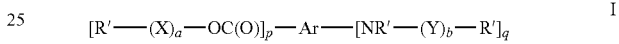

wherein:

Ar is an aromatic ring substituted with 1, 2, or 3 R groups;

X is independently at each occurrence selected from:
—$CH_2COO$— (glycolic acid moiety);
—$CH(CH_3)COO$— (lactic acid moiety);
—$CH_2CH_2OCH_2COO$— (dioxanone moiety);
—$CH_2CH_2CH_2CH_2CH_2COO$— (caprolactone moiety);
—$(CH_2)_yCOO$— where y is independently selected from 2, 3, 4, 6, 7, 8, 9, 10, 11, 12, 13, 14, 15, 16, 17, 18, 19, 20, 21, 22, 23, and 24; and,
—$(CH_2CH_2O)_zCH_2COO$— where z is independently selected from 2, 3, 4, 5, 6, 7, 8, 9, 10, 11, 12, 13, 14, 15, 16, 17, 18, 19, 20, 21, 22, 23, and 24;

Y is independently at each occurrence selected from:
—$COCH_2O$— (glycolic ester moiety);
—$COCH(CH_3)O$— (lactic ester moiety);
—$COCH_2OCH_2CH_2O$— (dioxanone ester moiety);
—$COCH_2CH_2CH_2CH_2CH_2O$— (caprolactone ester moiety);
—$CO(CH_2)_mO$— where m is selected from 2, 3, 4, 6, 7, 8, 9, 10, 11, 12, 13, 14, 15, 16, 17, 18, 19, 20, 21, 22, 23, and 24; and,
—$COCH_2O(CH_2CH_2O)_n$— where n is selected from 2, 3, 4, 5, 6, 7, 8, 9, 10, 11, 12, 13, 14, 15, 16, 17, 18, 19, 20, 21, 22, 23, and 24;

R' is selected from hydrogen, benzyl, and $C_{1-6}$ alkyl;

p and q are independently selected from 0, 1, 2, 3, and 4, provided that p+q total 2, 3, or 4;

a and b, are independently selected from 0, 1, 2, 3, and 4, provided that a+b total from 1, 2, 3, 4, 5, or 6;

R is independently selected from —O—$(X)_c$—R' and —O—$(Y)_c$—R';

c is independently selected from 0, 1, 2, 3, and 4;

alternatively, R is independently selected from H, =O, O-glycosides, —$(CH_2)_{0-2}$—$OR^a$, —$(CH_2)_{0-2}$—$C_6H_5$, —$(CH_2)_{0-2}$—CHO, Cl, F, Br, I, —$(CH_2)_{0-2}$—OC(O)—$R^a$, —$(CH_2)_{0-2}$—$CO_2$—$R^a$, —$(C(CH_3))_{0-2}$—$CO_2$—$R^a$, —$(CH_2)_{1-2}$—$CO_2$—$(CH_2)_{1-2}$—$CO_2$—$R^a$, —$C(CH_3))_{1-2}$—$CO_2$—$(CH_2)_{1-2}$—$CO_2$—$R^a$, —$(CH_2)_{0-2}$—CO—$R^a$, —$O(CH_2)_{0-2}$—$C_6H_5$, —$O(CH_2)_{1-2}$—$CO_2$—$R^a$, —O(C (CH₃))₁₋₂—CO₂—Rᵃ,                    —O(CH₂)₁₋₂—CO—Rᵃ,
—(CH₂)₀₋₂—NO₂, —(CH₂)₀₋₂—NRᵃRᵃ, —(CH₂)₀₋₂—NRᵃ-
CORᵃ,    —(CH₂)₁₋₂—NRᵃC(O)(CH₂)₁₋₂ORᵃ,    —C₆H₅,
—C₆H₅ORᵃ, and —C₆H₅—CH=CHCO₂Rᵃ; and, Rᵃ is independently selected from H and C₁₋₆ alkyl.

Additional examples of p and q include (a) 0, 1, 2, and 3, provided that p+q total 1, 2, or 3; and (b) 0, 1, and 2, provided that p+q total 1, 2, or 3.

Additional examples of a and b include (a) 0, 1, 2, and 3, provided that a+b total from 1, 2, 3, or 4; and (b) 0, 1, and 2, provided that a+b total from 1, 2, or 3.

Additional examples of c include (a) 0, 1, 2, and 3; and (b) 0, 1, and 2.

The group represented by X is attached via its carbon terminus to the oxygen group of the carboxyl. The group represented by Y is attached via its carbonyl terminus to the oxygen or nitrogen group of the amino group.

The rate of hydrolysis of the difunctionalized aromatic compounds will depend upon a number of factors, including the functionalization species used and the number of functionalization species present on the difunctionalized aromatic (e.g., 1-6). Glycolic acid modified aromatics should hydrolyze faster than dioxanone modifies ones, where as lactic acid and caprolactone modified aromatics should take much longer to hydrolyze than glycolic acid and dioxanone modified aromatics. Furthermore, it is expected that the rate of hydrolysis will increase with the increase in the value of p and q. Thus, the desired time range may be obtained by altering the number and type of functionalization species used to functionalize the aromatics.

The present invention also provides novel difunctionalized aromatic compounds of formula I, wherein:
y is independently selected from 2, 3, and 4;
z is independently selected from 2, 3, and 4;
p is independently selected from 1, 2, and 3; and,
q is selected from 1, 2, and 3.

The present invention also provides novel difunctionalized aromatic compounds of formula I, wherein:
X is independently at each occurrence selected from:
—CH₂COO—;
—CH(CH₃)COO—;
—CH₂CH₂OCH₂COO—; and,
—CH₂CH₂CH₂CH₂CH₂COO—; and,
Y is independently at each occurrence selected from:
—COCH₂O—;
—COCH(CH₃)O—;
—COCH₂OCH₂CH₂O—;
—COCH₂CH₂CH₂CH₂CH₂O—;
p and q are independently selected from 0, 1, 2, and 3, provided that p+q total 2 or 3;
a and b, are independently selected from 0, 1, 2, and 3, provided that a+b total from 1, 2, 3, or 4; and,
c is independently selected from 0, 1, 2, and 3.

The present invention also provides novel difunctionalized aromatic compounds of formula I, wherein: X is selected from:
X is independently at each occurrence selected from: —CH₂COO— and —CH(CH₃)COO—;
Y is independently at each occurrence selected from: —COCH₂O— and —COCH(CH₃)O—;
a and b, are independently selected from 0, 1, and 2, provided that a+b total 1, 2, 3, or 4; and,
c is independently selected from 0, 1, and 2.

The present invention also provides novel difunctionalized aromatic compounds of formula Ia-Ic:

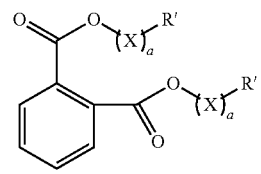

Ia

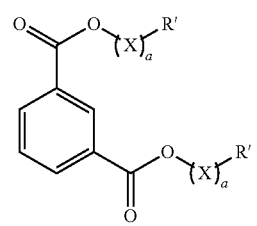

Ib

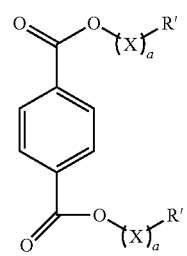

Ic

The present invention also provides novel difunctionalized aromatic compounds of formula IIa-IIc:

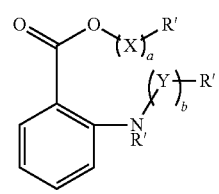

IIa

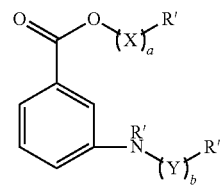

IIb

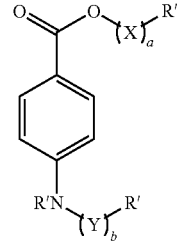

IIc

The present invention also provides novel difunctionalized aromatic compounds of formula IIIa-IIIc:

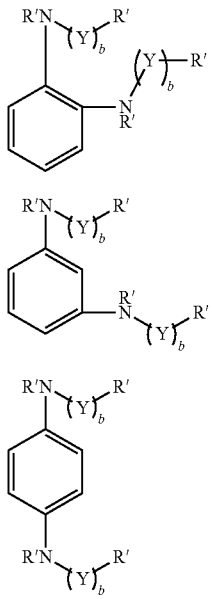

The present invention also provides a blend comprising one or more of the functionalization species with one or more species of aromatic compounds.

The present invention also provides polymers formed from the difunctionalized aromatic compounds of this invention that are difunctional, that is those species having more than one hydroxyl, carboxyl, ester, amino, cyano, or other polymerizable group. If the difunctionalized aromatic of the present invention only has one polymerizable moiety, then it can only be used as an endcap. Polymers of the difunctionalized aromatic compounds are expected to have specific ranges over which they release the active aromatic moiety. One can blend polymers made from difunctionalized aromatic compounds derived from one or more of the functionalization species and one or more species of aromatic moieties to obtain the release range desired for the specific application into the body of a mammalian, including a human or the environment. This release range varies with the species used for functionalization as well as the aromatic compound. The combinations or blends of these entities may comprise an amount of from 0.5% to 99.5% by weight of each species.

In addition, the monomers of the present invention may be polymerized to form absorbable polymers that display excellent physical, chemical, and biological properties, which make them useful in medical applications. The polymers of the present invention are expected to form non-toxic degradation products by hydrolytic chain cleavage under physiological conditions. The novel polymers of the present invention are expected to have increased rate of degradation and bioresorption as well as controllable degradation profile in comparison to the currently available polymers.

For example, a phenol, such as resorcinol, can be functionalized to form a reactive compound, which can be polymerized to form an absorbable polymer with a specific absorption profile. Similarly, each the aromatics described above can be functionalized to form reactive monomers. The polymers derived from these monomers will have unique physical and biological properties with absorption profiles that are controllable.

Thus, the present invention provides novel polymers formed from difunctionalized aromatic compounds of formula I.

The difunctionalized aromatic compounds of the present invention can be polymerized via conventional polymerization process using diol, triols, dicarboxylic acids, tricarboxylic acids, diamines, or triamines based on the starting difunctionalized or trifunctionalized aromatics, including those processes that synthesize polymers traditionally considered hydrolytically stable and non-biodegradable.

The present invention encompasses a variety of different polymers, some of which are copolymers. The polymers of the present invention include (a) polymers formed from one functionalized aromatic; (b) copolymers formed from more than one (e.g., 2, 3, or 4) type of difunctionalized aromatic (e.g., a blend of difunctionalized aromatic compounds that is polymerized); (c) copolymers formed from at least one type of difunctionalized aromatic having at least two active sites (e.g, 2 or 3) and a difunctional molecule (e.g., dicarboxylic acids, dialcohols, diisocyanates, amino-alcohols, hydroxycarboxylic acids, and diamines); and (d) copolymers formed from at least one of the polymers of (a)-(c) and at least one lactone monomer (e.g., glycolide, lactide, ε-caprolactone, trimethylene carbonate, and p-dioxanone). The absorption profile of the polymers of the present invention will depend upon a number of factors, including the functionalization species used and the number of functionalization species present on the difunctionalized aromatic (e.g., 1-6). Glycolic acid based polymers should hydrolyze faster than dioxanone based, where as lactic acid and caprolactone based polymers should take much longer to hydrolyze than glycolic acid and dioxanone based polymers. The desired time range may be obtained by altering the number and type of functionalization species as well as the number of different difunctionalized aromatic compounds (e.g., a blend of two or more functionalized aromatics). The desired time range will also be impacted by moieties used for co-polymerization (e.g., difunctional compounds or lactone monomers).

The difunctionalized aromatic polymers can be used in various medical applications described herein or can be further polymerized with lactone monomers, such as glycolide, lactide, ε-caprolactone, trimethylene carbonate, and p-dioxanone, and the resulting absorbable functionalized aromatic/lactone copolymers can be used in the various medical applications described herein.

As noted above, more than one of the difunctionalized aromatic compounds of the present invention can be blended and polymerized to form a difunctionalized aromatic copolymer. The difunctionalized aromatic copolymers can be used in various medical applications described herein or can be further polymerized with lactone monomers, such as glycolide, lactide, ε-caprolactone, trimethylene carbonate, and p-dioxanone, and the resulting absorbable polymers can also have the medical applications described herein.

As noted above, the difunctionalized aromatic compounds of the present invention with at least two reactive sites can be polymerized with difunctional molecules (e.g., dicarboxylic acids, dialcohols, diisocyanates, amino-alcohols, hydroxycarboxylic acids, and diamines) to form absorbable polymers, including but not limited to polyesters, polyester amides, polyurethanes, polyamides, and polyanhydrides by simple polycondensation reactions. The functionalized aromatic/difunctional molecule polymers can be used in various medical applications or can be further polymerized with lactone monomers, such as glycolide, lactide, ε-caprolactone, trimethylene carbonate, and p-dioxanone, and the resulting absorbable polymers potential have the medical applications described above.

In another example of the present invention, functionalized dihydroxy aromatic compounds of the present invention can be used in the preparation of polyester amides by reacting with dicarboxylic acid compounds. Dicarboxylic acids useful in the present invention have the following structure:

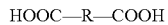
HOOC—R—COOH wherein R is selected from saturated and unsaturated, substituted and unsubstituted alkyl, aryl and alkylaryl groups having from 1, 2, 3, 4, 5, 6, 7, 8, 9, 10, 11, 12, 13, 14, 15, 16, 17, and 18 carbon atoms In another example of the present invention, functionalized dicarboxylic acid aromatic compounds of the present invention can be used in the preparation of polyesters by reacting with the dialcohol (i.e., diol) compounds. Dialcohols useful in the present invention have the following structure:

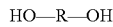
HO—R—OH wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms. Alternatively, polyalkylene oxides have weight average molecular weights from about 500-5,000 can be used as a diol (i.e., a polydiol). Suitable diols or polydiols for use in the present invention are diol or diol repeating units with up to 8 carbon atoms. Examples of suitable diols include 1,2-ethanediol (ethylene glycol); 1,2-propanediol (propylene glycol); 1,3-propanediol; 1,4-butanediol; 1,5-pentanediol; 1,3-cyclopentanediol; 1,6-hexanediol; 1,4-cyclohexanediol; 1,8-octanediol; and, combinations thereof. Examples of polydiols include polyethylene glycol and polypropylene glycol with weight average molecular weights of 500-5000.

In another example of the present invention, functionalized dihydroxy aromatic compounds of the present invention can be used in the preparation of polyurethanes by reacting with diisocyante compounds. Examples of diisocyanates include hexamethylene diisocyante, lysine diisocyanate, methylene diphenyl diisocyanate (e.g., MDI), hydrogenated MDI (e.g., methylene dicyclohexyl diisocyanate), and isophorone diisocyanate.

In another example of the present invention, functionalized hydroxy-amino aromatic compounds of the present invention can be used in the preparation of polyesteramides by reacting with dicarboxylic acid compounds described above.

In another example of the present invention, functionalized dicarboxylic acid aromatic compounds of the present invention can be used in the preparation of polyesteramides by reacting with the amino-alcohol compounds. Amino-alcohols useful in the present invention have the following structure:

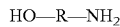
HO—R—NH₂ wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms.

In another example of the present invention, functionalized hydroxy-carboxylic acid aromatic compounds of the present invention can be used in the preparation of polyesters by reacting with hydroxycarboxylic acid compounds. Hydroxycarboxylic acids useful in the present invention have the following structure:

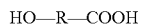
HO—R—COOH wherein R is selected from saturated and unsaturated, substituted and unsubstituted alkyl, aryl and alkylaryl groups having from 1, 2, 3, 4, 5, 6, 7, 8, 9, 10, 11, 12, 13, 14, 15, 16, 17, and 18 carbon atoms, In another example of the present invention, functionalized amino-carboxylic acid aromatic compounds of the present invention can be used in the preparation of polyesteramides by reacting with the hydroxycarboxylic acid compounds described above.

In another example of the present invention, functionalized dicarboxylic acid aromatic compounds of the present invention can be used in the preparation of polyamides by reacting with the diamine compounds. Diamines useful in the present invention have the following structure:

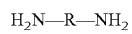
H₂N—R—NH₂ wherein R is selected from saturated and unsaturated, substituted and unsubstituted alkyl, aryl and alkylaryl groups having from 2, 3, 4, 5, 6, 7, 8, 9, 10, 11, 12, 13, 14, 15, 16, 17, and 18 carbon atoms. Alternatively, polyalkylene oxides that are diamines with weight average molecular weights from about 500-5,000 can be used.

In another example of the present invention, functionalized dicarboxylic acid aromatic compounds of the present invention can be used in the preparation of polyanhydrides by reacting with the dicarboxylic acid compounds described above.

The difunctionalized aromatic compounds of the present invention having more than two reactive groups (e.g., 3) are expected to be useful in the preparation of cross linked hydrogels and are prepared Examples of polymers of the present invention have weight-average molecular weights above about 20,000 daltons or above about 100,000 daltons, calculated from gel permeation chromatography (GPC) relative to polystyrene standards in tetrahydrofuran (THF) without further correction.

The polymers of the present invention should be able to be processed by known methods commonly employed in the field of synthetic polymers to provide a variety of useful articles with valuable physical and chemical properties. The useful articles can be shaped by conventional polymer-forming techniques such as extrusion, compression molding, injection molding, solvent casting, and wet spinning. Shaped articles prepared from the polymers are expected to be useful as degradable devices for medical implant applications.

The present invention also relates to a composition, comprising: at least two (e.g., 2, 3, 4, or 5) functional aromatic compounds of the present invention.

The present invention also relates to a composition, comprising: at least one functionalized aromatic, wherein the composition is suitable for use as at least one of the following: (a) a solvent for drugs; (b) a nutritional compound; (c) a cosmetic: and, (d) a pharmaceutical. Each of the compositions may further comprise an additional component suitable for such composition. For example, when the composition is suitable for use as a cosmetic it may further comprise: one or more cosmetic ingredients. Also, when the composition is suitable for use as a pharmaceutical it may further comprise: one or more pharmaceutically acceptable excipients. In addition, each of the compositions may comprise a difunctionalized aromatic derived from a aromatic having a property useful to that type of composition. For example, the starting aromatic may be (a) a nutritional supplement or a food intermediary; (b) an anticancer agent; (c) an antimicrobial agent;

(d) an anti-inflammatory agent; (e) a pain-reducer; and, (f) an antioxidant agent. Also, the compositions may further comprise one of agents (a)-(f).

The compositions of the present invention may be suitable for administration via a route selected from oral, enteral, parenteral, topical, transdermal, ocular, vitreal, rectal, nasal, pulmonary, and vaginal.

The implantable medical devices of the present invention, comprise: at least one absorbable polymer of the present invention. For example, a polymer of the present invention can be combined with a quantity of a biologically or pharmaceutically active compound sufficient to be therapeutically effective as a site-specific or systemic drug delivery system (see Gutowska et al., J. Biomater. Res., 29, 811-21 (1995) and Hoffman, J. Controlled Release, 6, 297-305 (1987)). Another example of the present invention is a method for site-specific or systemic drug delivery by implanting in the body of a patient in need thereof an implantable drug delivery device comprising a therapeutically effective amount of a biologically or a physiologically active compound in combination with at least one absorbable polymer of the present invention.

In another example, at least one polymer of the present invention is formed into a porous device (see Mikos et al., Biomaterials, 14, 323-329 (1993) or Schugens et al., J. Biomed. Mater. Res., 30, 449-462 (1996)) to allow for the attachment and growth of cells (see Bulletin of the Material Research Society, Special Issue on Tissue Engineering (Guest Editor: Joachim Kohn), 21(11), 22-26 (1996)). Thus, the present invention provides a tissue scaffold comprising a porous structure for the attachment and proliferation of cells either in vitro or in vivo formed from at least one absorbable polymer of the present invention The present invention also relates to an article (e.g., an implantable medical device), comprising: a metal or polymeric substrate having thereon a coating, wherein the coating, comprises: at least one polymer of the present invention.

The present invention also relates to a molded article prepared from at least one polymer of the present invention.

The present invention also relates to a controlled drug delivery system, comprising: at least one polymer of the present invention physically admixed with a biologically or pharmacologically active agent. For example, the controlled drug delivery system can comprise: a biologically or pharmacologically active agent coated with at least one polymer of the present invention.

The present invention also relates to a controlled drug delivery system, comprising: a biologically or pharmacologically active agent physically embedded or dispersed into a polymeric matrix formed from at least one polymer of the present invention.

The present invention also relates to a tissue scaffold having a porous structure for the attachment and proliferation of cells, either in vitro or in vivo, formed from one least one polymer of the present invention.

The present invention also relates to a composition, comprising: at least one polymer of the present invention, which has been further polymerized with at least one lactone monomer selected from: glycolide, lactide, p-dioxanone, trimethylene carbonate, and caprolactone.

The present invention also relates to an implantable biomedical device, comprising: at least one polymer that has been further polymerized with at least one lactone monomer.

The present invention also relates to a biodegradable chewing gum composition, comprising: an effective amount of at least one polymer that has been further polymerized with at least on lactone monomer.

The present invention also relates to an article (e.g., an implantable medical device), comprising: a metal or polymeric substrate and having thereon a coating, wherein said coating comprises at least one polymer that has been further polymerized with at least one lactone monomer.

The present invention also relates to a molded article prepared from at least one polymer that has been further polymerized with at least one lactone monomer.

The present invention also relates to a monofilament or multifilament prepared from at least one polymer that has been further polymerized with at least one lactone monomer.

The present invention also relates to a controlled drug delivery system, comprising: at least one polymer that has been further polymerized with at least one lactone monomer, which has been physically admixed with a biologically or pharmacologically active agent.

The present invention also relates to a controlled drug delivery system, comprising: a biologically or pharmacologically active agent physically embedded or dispersed into a polymeric matrix formed from at least one polymer that has been further polymerized with at least one lactone monomer.

The present invention also relates to a tissue scaffold having a porous structure for the attachment and proliferation of cells, either in vitro or in vivo, formed from at least one polymer that has been further polymerized with at least one lactone monomer.

The present invention also relates to low molecular weight polymers or oligomers of the difunctionalized aromatic compounds of the present invention that are further reacted to form reactive end groups (e.g., isocyanates, expoxides, and acrylates). Low-molecular weight polymers or oligomers as used herein means a polymer having a number average molecular weight of about 500-20,000 or 500-10,000. For example, some of the difunctionalized aromatic compounds behave chemically like diols. They can be reacted with dicarboxylic acids to form polyesters, which are usually hydroxyterminated. These hydroxyterminated oligomers can be further reacted to form isocyanates, epoxides and acrylates. Similarly the difunctionalized aromatic compounds can be reacted with isocyanates to make urethanes. Thus, the present invention also includes a composition, comprising: at least one polymer of the present invention, which has been further reacted to form reactive end groups.

The present invention also relates to polymers made from difunctionalized aromatic compounds that have been sterilized by cobalt-60 radiation, electron beam radiation, and/or ethylene oxide.

"Bioabsorbable" or "absorbable" as used herein means that the material readily reacts or enzymatically degrades upon exposure to bodily tissue for a relatively short period of time, thereby experiencing a significant weight loss in that short period of time. Complete bioabsorption/absorption should take place within twelve months, although it may be complete within nine months or within six months. In this manner, the polymers of the present invention can be fabricated into medical and surgical devices, which are useful for a vast array of applications requiring complete absorption within a relatively short time period.

The biological properties of the bioabsorbable polymers of the present invention used to form a device or part thereof, as measured by its absorption rate and its breaking strength retention in vivo (BSR), can be varied to suit the needs of the particular application for which the fabricated medical device or component is intended. This can be conveniently accomplished by varying the ratio of components of the polymer chosen.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methanesulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluenesulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 18th ed., Mack Publishing Company, Easton, Pa., 1990, p 1445, the disclosure of which is hereby incorporated by reference.

"Therapeutically effective amount" includes an amount of a compound of the present invention that is effective when administered alone or in combination to treat the desired indication.

"Alkyl" includes both branched and straight-chain saturated aliphatic hydrocarbon groups having the specified number of carbon atoms. $C_{1-6}$ alkyl, for example, includes $C_1$, $C_2$, $C_3$, $C_4$, $C_5$, and $C_6$ alkyl groups. Examples of alkyl include methyl, ethyl, n-propyl, i-propyl, n-butyl, s-butyl, t-butyl, n-pentyl, s-pentyl, and n-hexyl.

Polymers of the present invention may be made in the form of random copolymers or block copolymers. A coupling agent may also be added to the polymers of the present invention. A coupling agent is a reagent that has a least two functional groups that are capable of covalently bonding to two different monomers. Examples of coupling agents include trifunctional or tetrafunctional polyols, oxycarboxylic acids, and polybasic carboxylic acids (or acid anhydrides thereof). Other coupling agents include the difunctional groups (e.g., diols, diacids, diamines, and hydroxy-acids) previously discussed. The addition of the coupling agents causes the branching of long chains, which can impart desirable properties in the molten state to the pre-polymer. Examples of polyfunctional coupling agents include trimethylol propane, glycerin, pentaerythritol, malic acid, citric acid, tartaric acid, trimesic acid, propane tricarboxylic acid, cyclopentane tetracarboxylic anhydride, and combinations thereof.

A "pre-polymer" is a low-molecular weight polymer, as previously defined, that have reactive endgroups (e.g., hydroxy groups) that can be further reactive with, for example, the lactone monomers.

The amount of coupling agent to be added before gelation occurs is a function of the type of coupling agent used and the polymerization conditions of the polymer or molecular weight of the pre-polymer to which it is added. Generally in the range of from about 0.1 to about 10 mole percent of a trifunctional or a tetrafunctional coupling agent may be added based on the moles of polymers present or anticipated from the synthesis.

The polymerization of a polyester of the present invention can be performed under melt polycondensation conditions in the presence of an organometallic catalyst at elevated temperatures. The organometallic catalyst can be a tin-based catalyst (e.g., stannous octoate or dibutyl tin oxide). The catalyst can be present in the mixture at a mole ratio of diol, dicarboxylic acid, and optionally lactone monomer to catalyst will be in the range of from about 15,000/1 to 80,000/1. The reaction can be performed at a temperature not less than about 120° C. under reduced pressure. Higher polymerization temperatures may lead to further increases in the molecular weight of the copolymer, which may be desirable for numerous applications. The exact reaction conditions chosen will depend on numerous factors, including the properties of the polymer desired, the viscosity of the reaction mixture, and the glass transition temperature and softening temperature of the polymer. Desired reaction conditions of temperature, time and pressure can be readily determined by assessing these and other factors. Generally, the reaction mixture will be maintained at about 220° C. The polymerization reaction can be allowed to proceed at this temperature until the desired molecular weight and percent conversion is achieved for the copolymer, which will typically take about 15 minutes to 24 hours. Increasing the reaction temperature generally decreases the reaction time needed to achieve a particular molecular weight.

Polymerization conditions for the preparation of other types of polymers of the present invention (e.g., polyamides) are described in the literature. Those skilled in the art will recognize that the polymers described herein can be made from known procedures.

Copolymers of the absorbable polymers of the present invention can be prepared by preparing a pre-polymer under melt polycondensation conditions, then adding at least one lactone monomer or lactone pre-polymer. The mixture could then be subjected to the desired conditions of temperature and time to copolymerize the pre-polymer with the lactone monomers.

A lactone pre-polymer is a pre-polymer formed by ring opening polymerization with a known initiator (e.g., ethylene glycol, diethylene glycol, glycerol, or other diols or triols).

The molecular weight of the pre-polymer as well as its composition can be varied depending on the desired characteristic, which the pre-polymer is to impart to the copolymer. For example, the pre-polymers of the present invention, from which the copolymer is prepared, generally have a molecular weight that provides an inherent viscosity between about 0.2 to about 2.0 deciliters per gram (dl/g) as measured in a 0.1 g/dl solution of hexafluoroisopropanol at 25° C. Those skilled in the art will recognize that the pre-polymers described herein can also be made from mixtures of more than one diol or dicarboxylic acid.

One of the beneficial properties of the polyesters of the present invention is that the ester linkages are hydrolytically unstable, and therefore the polymer is bioabsorbable because it readily breaks down into small segments when exposed to moist bodily tissue. In this regard, while it is envisioned that co-reactants could be incorporated into the reaction mixture of the dicarboxylic acid and the diol for the formation of the polyester pre-polymer, it is preferable that the reaction mixture does not contain a concentration of any co-reactant which would render the subsequently prepared polymer nonabsorbable. The reaction mixture can be substantially free of any such co-reactants if the presence thereof results in a nonabsorbable polymer.

The polymers of the present invention can be melt processed by numerous methods to prepare a vast array of useful devices. These polymers can be injection or compression molded to make implantable medical and surgical devices, especially wound closure devices.

Alternatively, the polymers can be extruded to prepare fibers. The filaments thus produced may be fabricated into sutures or ligatures, attached to surgical needles, packaged, and sterilized by known techniques. The polymers of the present invention may be spun as multifilament yarn and woven or knitted to form sponges or gauze, (or non-woven sheets may be prepared) or used in conjunction with other molded compressive structures as prosthetic devices within the body of a human or animal where it is desirable that the structure have high tensile strength and desirable levels of compliance and/or ductility. Examples include tubes, including branched tubes, for artery, vein, or intestinal repair, nerve splicing, tendon splicing, sheets for typing up and supporting damaged surface abrasions, particularly major abrasions, or areas where the skin and underlying tissues are damaged or surgically removed.

Additionally, the polymers can be molded to form films which, when sterilized, are useful as adhesion prevention barriers. Another alternative processing technique for the polymers of the present invention includes solvent casting, particularly for those applications where a drug delivery matrix is desired.

The polymers of the present invention can be used to coat a surface of a surgical article to enhance the lubricity of the coated surface. The polymer may be applied as a coating using conventional techniques. For example, the polymer may be solubilized in a dilute solution of a volatile organic solvent (e.g. acetone, methanol, ethyl acetate, or toluene), and then the article can be immersed in the solution to coat its surface. Once the surface is coated, the surgical article can be removed from the solution where it can be dried at an elevated temperature until the solvent and any residual reactants are removed.

For coating applications, the polymer should exhibit an inherent viscosity, as measured in a 0.1 gram per deciliter (g/dl) of hexafluoroisopropanol (HFIP), between about 0.05-2.0 dl/g or about 0.10-0.80 dl/g. If the inherent viscosity were less than about 0.05 dl/g, then the polymer may not have the integrity necessary for the preparation of films or coatings for the surfaces of various surgical and medical articles. On the other hand, it is possible to use polymers with an inherent viscosity greater than about 2.0 dl/g, though it may be difficult to do so.

Although numerous surgical articles (including but not limited to endoscopic instruments) can be coated with the polymer of the present invention to improve the surface properties of the article, specific surgical articles include surgical sutures, stents, and needles. For example the surgical article can be a suture, which can be attached to a needle. The suture can be a synthetic absorbable suture. These sutures are derived, for example, from homopolymers and copolymers of lactone monomers such as glycolide, lactide, $\epsilon$-caprolactone, 1,4-dioxanone, and trimethylene carbonate. The suture can be a braided multifilament suture composed of polyglycolide or poly(glycolide-co-lactide).

The amount of coating polymer to be applied on the surface of a braided suture can be readily determined empirically, and will depend on the particular copolymer and suture chosen. Ideally, the amount of coating copolymer applied to the surface of the suture may range from about 0.5-30 percent of the weight of the coated suture or from about 1.0-20 weight percent, or from 1-5 percent by weight. If the amount of coating on the suture were greater than about 30 weight percent, then it may increase the risk that the coating may flake off when the suture is passed through tissue Sutures coated with the polymers of the present invention are desirable because they have a more slippery feel, thus making it easier for the surgeon to slide a knot down the suture to the site of surgical trauma. In addition, the suture is more pliable, and therefore is easier for the surgeon to manipulate during use. These advantages are exhibited in comparison to sutures which do not have their surfaces coated with the polymer of the present invention.

When the article of the present invention is a metal stent, the amount of coating applied to the surface of the article is an amount which creates a layer with a thickness ranging, for example, between about 2-20 microns on the stent or about 4-8 microns. If the amount of coating on the stent were such that the thickness of the coating layer was greater than about 20 microns, or if the thickness was less than about 2 microns, then the desired performance of the stent as it is passed through tissue may not be achieved.

When the article of the present invention is a surgical needle, the amount of coating applied to the surface of the article is an amount which creates a layer with a thickness ranging, for example, between about 2-20 microns on the needle or about 4-8 microns. If the amount of coating on the needle were such that the thickness of the coating layer was greater than about 20 microns, or if the thickness was less than about 2 microns, then the desired performance of the needle as it is passed through tissue may not be achieved.

The polymers of the present invention can also be used as a pharmaceutical carrier in a drug delivery matrix. To form this matrix the polymer can be mixed with a therapeutic agent to form the matrix. There are a variety of different therapeutic agents, which can be used in conjunction with the polymers of the invention. In general, therapeutic agents which may be administered via the pharmaceutical compositions of the invention include, antiinfectives such as antibiotics and antiviral agents; analgesics and analgesic combinations; anorexics; antihelmintics; antiarthritics; antiasthmatic agents; anticonvulsants; antidepressants; antidiuretic agents; antidiarrheals; antihistamines; antiinflammatory agents; antimigraine preparations; antinauseants; antineoplastics; antiparkinsonism drugs; antipruritics; antipsychotics; antipyretics, antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary, peripheral and cerebral; central nervous system stimulants; cough and cold preparations, including decongestants; hormones such as estradiol and other steroids, including corticosteroids; hypnotics; immunosuppressives; muscle relaxants; parasympatholytics; psychostimulants; sedatives; and tranquilizers; and naturally derived or genetically engineered proteins, polysaccharides, glycoproteins, or lipoproteins.

The drug delivery matrix may be administered in any suitable dosage form including orally, parenterally, subcutaneously as an implant, vaginally, or as a suppository. Matrix formulations containing the polymers of the present invention may be formulated by mixing one or more therapeutic agents with the polymer. The therapeutic agent, may be present as a liquid, a finely divided solid, or any other appropriate physical form. Typically, but optionally, the matrix will include one or more additives, e.g., nontoxic auxiliary substances such as diluents, carriers, excipients, or stabilizers. Other suitable additives may be formulated with the polymers of the present invention and pharmaceutically active agent. If water is to be used, then it can be useful to add it just before administration.

The amount of therapeutic agent will be dependent upon the particular drug employed and medical condition being treated. Typically, the amount of drug represents about 0.001%-70%, 0.001%-50%, or 0.001%-20% by weight of the matrix.

The quantity and type of polymer incorporated into a composition (e.g., parenterally delivered composition) will vary depending on the release profile desired and the amount of drug employed. The product may contain blends of polymers of the present invention to provide the desired release profile or consistency to a given formulation.

The polymers of the present invention, upon contact with body fluids including blood or the like, undergoes gradual degradation (mainly through hydrolysis) with concomitant release of the dispersed drug for a sustained or extended period (as compared to the release from an isotonic saline solution). This can result in prolonged delivery (e.g., over 1-2,000 hours or 2-800 hours) of effective amounts (e.g., 0.0001 mg/kg/hour to 10 mg/kg/hour) of the drug. This dosage form can be administered as is necessary depending on the subject being treated, the severity of the affliction, and the judgment of the prescribing physician.

Individual formulations of drugs and polymers of the present invention may be tested in appropriate in vitro and in vivo models to achieve the desired drug release profiles. For example, a drug could be formulated with a polymer of the present invention and orally administered to an animal. The drug release profile could then be monitored by appropriate means such as, by taking blood samples at specific times and assaying the samples for drug concentration. Following this or similar procedures, those skilled in the art will be able to formulate a variety of formulations.

The new difunctionalized aromatic compounds can have controllable hydrolysis profiles, improved bioavailability, improved efficacy and enhanced functionality. The difunctional compounds can readily polymerize into biodegradable polyesters, polyester amides, polyurethanes, polyamides, and polyanhydrides, for example, useful for many applications, including biomedical applications, foodstuffs, nutritional supplements, cosmetics, medicaments, coatings and others readily apparent to one skilled in the art.

An object of this invention is to combine these molecules, such as glycolic acid, lactic acid, p-dioxanone, ε-caprolactone, —(CH$_2$)$_y$COO—, where y is one of the integers 2,3,4 and between 6 and 24 inclusive, and —(CH$_2$CH$_2$O)$_z$CH$_2$COO—, where z is an integer between 2 and 24 inclusive, with aromatic compound, to form a new chemical entity. Preferential examples of functionalization molecules are glycolic acid, lactic acid, p-dioxanone, and ε-caprolactone. This functionalization enhances the native value of the aromatic compound by releasing the aromatic moiety by hydrolysis or degradation of the compound. The compound degrades under controllable conditions in the environment, in the body of an animal, for example a mammalian, including a human.

The glycolic acid moiety, lactic acid moiety, dioxanone moiety, caprolactone moiety, moieties of —(CH$_2$)$_y$COO— where y is one of the numbers 2,3,4 and 6-24, and moieties of —(CH$_2$CH$_2$O)$_z$CH$_2$COO— where z is an integer between 2 and 24, including 2 and 24, have different hydrolysis or degradation rates and times over which they release the active aromatic moiety and thus do the difunctionalized aromatic acid made from them. The species used for functionalization supplies the release time or range dictated by the application. Glycolic acid based compounds hydrolyze faster than p-dioxanone based, where as lactic acid and caprolactone based compounds take much longer to hydrolyze than glycolic acid and p-dioxanone based compounds. This desired time range may be obtained by using a combination of difunctionalized aromatic compounds, that is, a blend of two or more functionalized compounds made from any two or more of the species glycolide, lactide, dioxanone and polydioxanone combined with one aromatic compound.

The array of difunctionalized aromatic compounds developed as an aspect of the invention, have a wide range of hydrolysis rates that are controllable. The specific moiety or combination of moieties used for functionalization yields a compound or mixture with specific hydrolysis ranges.

The new difunctionalized aromatic compounds are expected to have more controllable hydrolysis profiles, improved bioavailability, improved efficacy and enhanced functionality. The difunctional compounds polymerize into biodegradable polymers, for example, useful for applications, including biomedical applications, foodstuffs, cosmetics, medicaments, coatings and other uses readily apparent to one skilled in the art.

Functionalization

The functionalized aromatic compounds of the present invention are typically prepared from a starting aromatic compound as shown below.

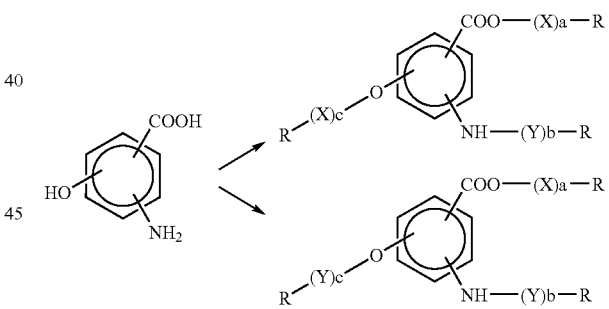

The desired X and Y groups can be added using methods known to those of skill in the art, some of which are described below.

Glycolic acid and lactic acid are also known as alpha hydroxy acids (AHA) present in fruits and other foods. These acids are present in many healthiest foods we eat and drink, and they are considered to be safe when used correctly. Glycolic acid occurs naturally as the chief acidic constituent of sugar cane juice and occurs in beet juice and unripe grapes. Its formula is HOCH$_2$COOH and is biodegradable. When glycolic acid is heated it readily loses water by self-esterification to form polyglycolic acid. Glycolic acid can function as both an acid and an alcohol. The process of attaching a glycolic acid moiety to the aromatic is defined as glycolation and will be referred to as such in describing this invention:

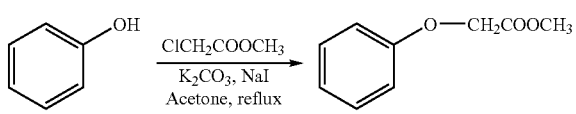

Aromatic carboxylic acid can be functionalized with glycolic acid moiety according to the following process:

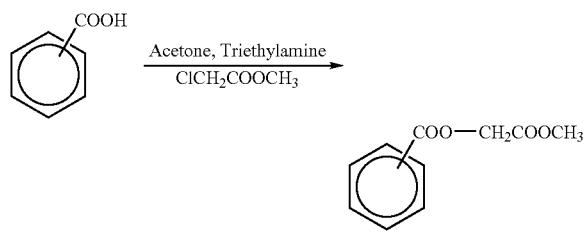

Lactic acid is a fermentation product of lactose. Lactic acid is produced commercially for use in foods and pharmaceuticals. Many surgical and orthopedic devices are made from polylactic acid. The process of attaching a lactic acid moiety to the aromatic compound is defined as lactolation and will be referred to as such in describing this invention:

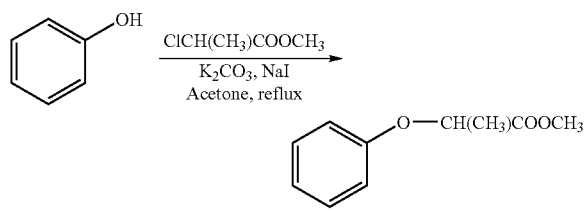

ε-Caprolactone is a cyclic monomer and is reactive, and the polymers derived are useful for tailoring specialty polyols and hydroxy-functional polymer resins with enhanced flexibility. The monomer polymerizes under mild conditions to give low viscosity products superior to conventional aliphatic polyesters. Copolymers of caprolactone with glycolide and lactide exhibit unique physical and biological properties as well as different hydrolysis profiles based on the composition of the monomers. The process of attaching an open chain ε-caprolactone moiety to the aromatic compound is defined as caprolation and will be referred to as such in describing this invention:

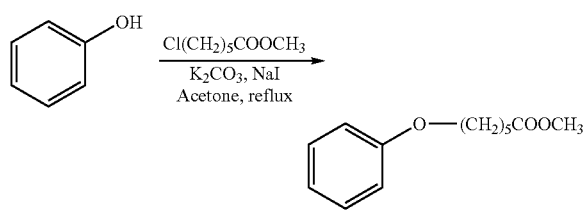

p-Dioxanone (1,4-dioxan-2-one) is a cyclic monomer and polymers are made via ring opening polymerization. Polyesters derived from this monomer are used in making absorbable surgical devices with longer absorption profile (slower hydrolysis) compare to polyglycolic acid. The absorbable surgical devices made from 1,4-dioxan-2-one are proved to be biologically safe, and biocompatible. The process of attaching an open chain p-dioxanone moiety (dioxanone) to the aromatic compound is defined as dioxonation and will be referred to as such in describing this invention:

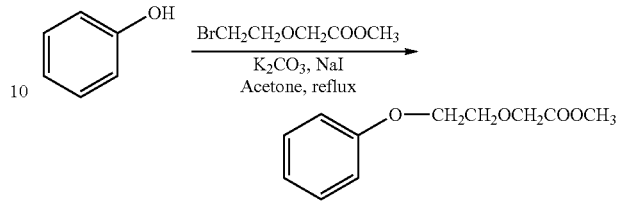

The difunctionalized aromatics of the present invention can be prepared according to any recognized method, including the Williamson ether synthesis.

Williamson Synthesis

Preparation of ethers is an important reaction for which a wide variety of procedures have been developed during the last 100 years. The most commonly used method for the preparation of symmetrical and unsymmetrical ethers is the Williamson synthesis, involving a halide and an alkoxide. It is possible to mix the halide and alcohol with solid KOH and DMSO. The reaction involves an SN2 reaction in which an alkoxide ion replaces a halogen, sulfonyl, or a sulfate group. Usually, alkyl halides are used. The alkoxide can be prepared by the reaction of the corresponding alcohol with an active metal such as metallic sodium or a metal hydride like NaH acting upon the alcohol. The resulting alkoxide salt is then reacted with the alkyl halide (sulfonate or sulfate) to produce the ether in an SN2 reaction.

Recently several new procedures for Williamson synthesis have developed in which the phase transfer catalysis (PTC) appear to very convenient and the reactions can be run under mild conditions with high yields. Most recently, it was reported that ethers could be prepared directly from alcohol and alkyl halides under microwave irradiation in the presence of a quaternary ammonium salt.

For the synthesis of aromatic ethers, the phenolic compound was reacted with one member of the group Na metal, NaH, and potassium carbonate to form a phenoxide and then reacted with an alkyl halide to form an aromatic ether as shown below:

The first step of the Williamson ether synthesis is the reaction of sodium hydride with a phenolic compound. Phenols are more acidic than alkanols because of resonance stabilization of the conjugated anion.

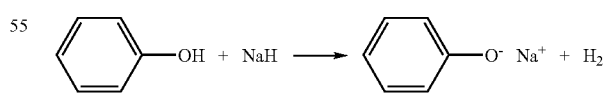

The resulting phenoxide ion is a powerful nucleophile, and reacts well with alkyl halide to form an ether.

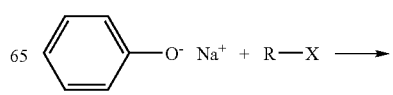

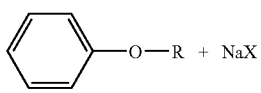

The alkyl halide should be primary so that the backside attack is not sterically hindered. When it is not primary, elimination usually results.

The general procedure for functionalizing phenolic compounds: to a mixture of phenolic compound, anhydrous potassium carbonate, sodium iodide, and disodium phosphate in anhydrous acetone, while refluxing, the alkyl halide is added and refluxed for a period of from a few hours to several days until the reaction is essentially complete. Then the acetone is distilled off, water is added, and crude product is filtered and recrystallized from a solvent or mixture of solvents. Some times the products are purified by column chromatography. Solvent systems, reaction conditions, and purification methods are modified based on the phenol compound.

The process of preparing a phenolic ester with glycolic acid is shown below:

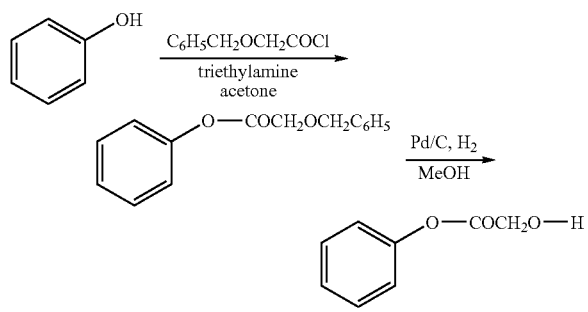

Benzyloxy acetyl chloride ($C_6H_5CH_2OCH_2COCl$) can be prepared as described in the following reaction scheme:

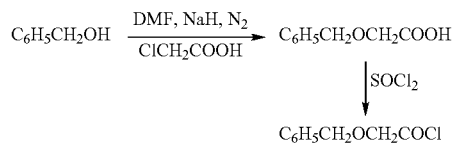

Using a similar method, $C_6H_5CH_2OCH(CH_3)COCl$, $C_6H_5CH_2O(CH_2)_5COCl$, and $C_6H_5CH_2OCH_2CH_2OCH_2COCl$ were synthesized for preparation of aromatic esters.

Lactic acid can function as both an acid and an alcohol. This dual functionality leads to a variety of chemical reactions and valuable physical properties. The process of preparing a phenolic ester with lactic acid is shown below:

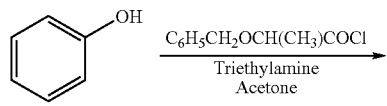

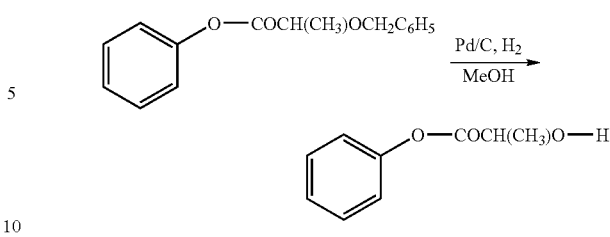

ε-Caprolactone, can function as both an acid and an alcohol. This dual functionality leads to a variety of chemical reactions and valuable physical properties. The process of preparing a phenolic ester with ε-caprolactone is shown below:

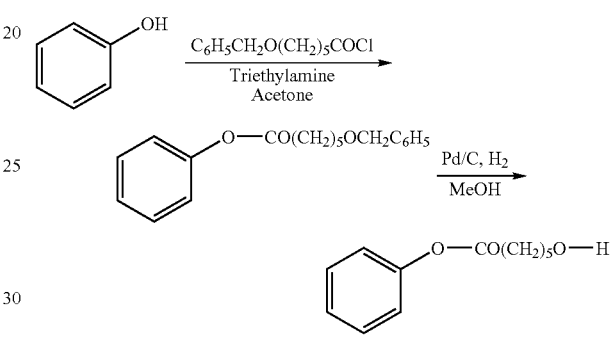

p-Dioxanone can function as both an acid and an alcohol. This dual functionality leads to a variety of chemical reactions and valuable physical properties. The process of preparing a phenolic ester with p-dioxanone is shown below:

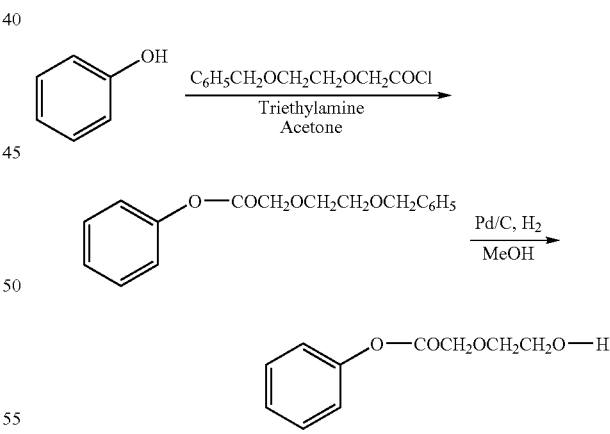

Synthesis of Phenolic Amides:

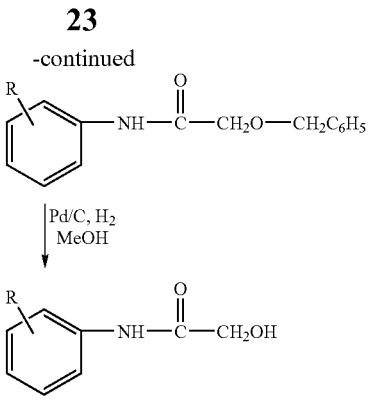

Benzyloxyamides are prepared by reacting benzyloxy acetic acid with an amine using dicyclohexylcarbodiimide (DCC) as coupling agent, in dichloromethane (DCM) as a solvent. The amine is dissolved in DCM and benzyloxyacetic acid is added. While maintaining below room temperature, DCC solution in DCM is added dropwise. The reaction generally proceeds cleanly for the formation of an amide. The urea formed is not soluble in DCM, and the urea can be filtered off to get the amide. In a second method the amines are reacted with the acid chloride directly using a base, such as $K_2CO_3$, $NaHCO_3$ or triethyl amine to neutralize the HCl that is formed during the reaction. Acetone is a good solvent for this reaction. Both methods are suitable for preparing benzyloxyamides.

Synthesis of Phenolic Esters:

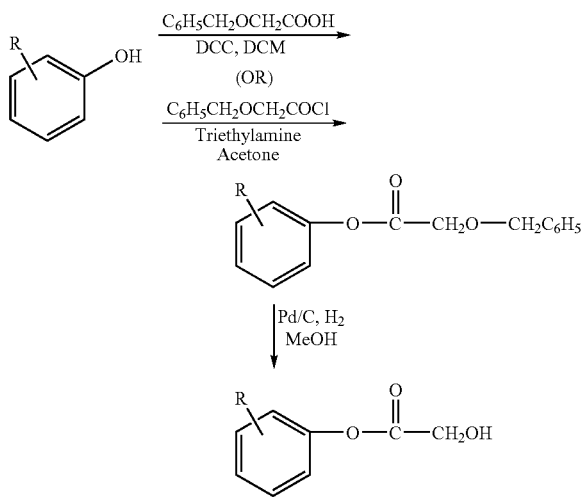

Conditions similar to those listed above can be used for preparing benzyloxyesters.

Debenzylation

Debenzylations were done using 50% wet Pd/C (5%) with hydrogen pressure up to 4 kg. MeOH or DMF can be as solvents. Dry Pd/C(5%) can be also used to avoid any moisture to avoid ester hydrolysis. DMF, MeOH, or Ethyl acetate can be used for this reaction.

Synthesis

The difunctionalized aromatic compounds can be prepared according to any recognized method, an example of which is shown below.

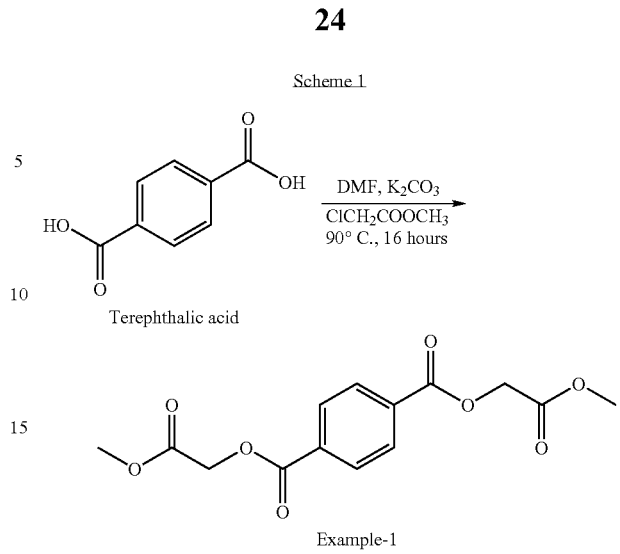

Bioactive Formulations

In other aspects of the present invention some difunctionalized aromatic compounds of the present invention can be further manufactured into formulations suitable for oral, rectal, parenteral (for example, subcutaneous, intramuscular, intradermal, or intravenous), transdermal, vitreal or topical administration. The most suitable route in any given case will depend on the nature and severity of the condition being treated and on the nature of the particular active compound that is being used. The formulations of a pharmaceutical composition are typically admixed with one or more pharmaceutically or veterinarially acceptable carriers and/or excipients as are well known in the art.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion.

Compositions of the present invention suitable for parenteral administration conveniently comprise sterile aqueous preparations of the active compounds, which preparations are preferably isotonic with the blood of the intended recipient.

Formulations suitable for rectal administration are preferably presented as unit dose suppositories.

Formulations suitable for ocular or vitreal administration may be presented as bioabsorbable coatings for implantable medical devices, injectables, liquids, gels or suspensions.

Formulations or compositions suitable for topical administration to the skin preferably take the form of an ointment, cream, lotion, paste, gel, spray, aerosol, or oil. Examples of carriers that conventionally used include Vaseline, lanoline, polyethylene glycols, alcohols, and combination of two or more thereof.

Formulations suitable for transdermal administration may be presented as discrete patches adapted to remain in intimate contact with the epidermis of the recipient for a prolonged period of time.

The active compounds may be provided in the form of foodstuffs or nutrition supplements, such as being added to, admixed into, coated, combined or otherwise added to a foodstuff. The term foodstuff is used in its widest possible sense and includes liquid formulations such as drinks including dairy products, biodegradable chewing gums, and other foods, such as health bars, desserts, etc. Food formulations containing compounds of the invention can be readily prepared according to standard practices.

Compounds of the formula used as medicaments or pharmaceuticals are typically administered in a manner and amount as is conventionally practiced. See, for example, Goodman and Gilman, *The Pharmaceutical Basis of Therapeutics*, current edition.

Compounds of the present invention may have potent antioxidant activity and increased acidity of their aromatic component, as well as the improved biodegradation provided by the functionalization, and thus find wide application in pharmaceutical and veterinary uses, in cosmetics such as more effective skin creams to prevent skin ageing, in sun screens, in foods, health drinks, nutritional supplements, shampoos, and the like.

Examples of difunctionalized aromatic compounds of the present invention are provided for some embodiments of the current invention. It can be extended to other species. This selection is not meant to limit the scope of the invention in any way. Other variations in the procedure may be readily apparent to those skilled in the art.

EXAMPLE 1

Terephthalic acid dimethoxycarbonylmethyl ester

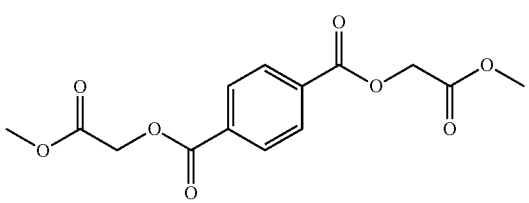

To a mixture of terephthalic acid (210 g, 1.264 mole), anhydrous $K_2CO_3$ (870 g, 6.295 mol) in anhydrous dimethyl formamide (2 L) at 90° C. was added methyl chloro acetate (312 g, 2.875 mol) drop wise and maintained 90° C. for 16 hours. Reaction mixture was cooled to room temperature and poured onto ice water (4 liter). The crude material was filtered, washed with 10% sodium bicarbonate and water, dried, and recrystallized from a mixture of chloroform:hexane (1:5) to give the purified title compound (85 g, 21.7%) as a white powder. M.p: 104.5-107° C. $^1$HNMR $(CDCl_3)$ δ 3.82 (s, 3H, ester), 4.88 (s, 2H,$OCH_2$), 8.18 (s,2H,Ar)

EXAMPLE 2

Terephthalic acid dimethoxycarbonylmethyl ester/ethylene glycol polymer

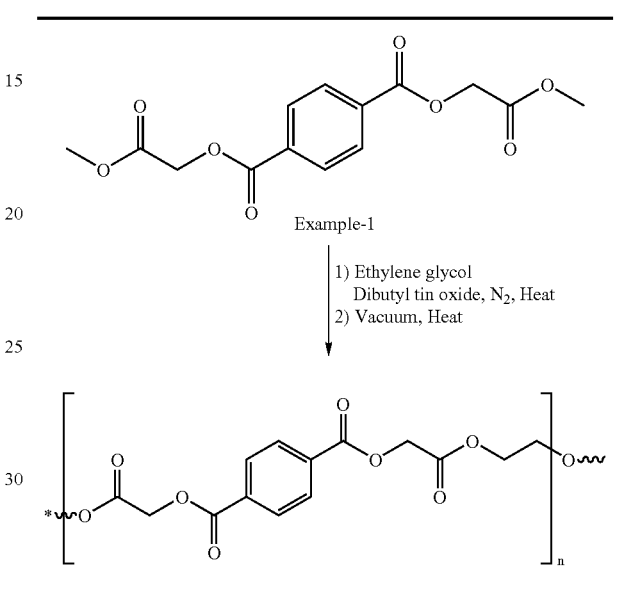

| Raw material | mw | Quantity | mmoles |
|---|---|---|---|
| | Batch-I | | |
| Example 1 | 310 | 10 g | 32.25 |
| Ethylene glycol | 62.07 | 6 g | 96.66 |
| Dibutyl tin oxide | 248.92 | 1 mg | 0.004 |

In to a clean dry 100 mL 4 neck round bottom flask equipped with nitrogen bubbler and distillation condenser were added terephthalic acid dimethoxy carbonyl methyl ester, ethylene glycol and dibutyl tin oxide under nitrogen atmosphere and heated as described below.

| Day-1 | |
|---|---|
| Bath 120° C. | 4 hours |
| Bath 140° C. | 16 hours |
| Day-2 | |
| Bath 160° C. | 23 hours |
| Heating was cut off and cooled to room temperature | |
| Day-3 | |
| High vacuum applied and heating started | |
| Bath 80° C. | 3 hours |
| Bath 90° C. | 2 hours |
| Heating cut off allowed to room temperature, removed vacuum and kept under nitrogen | |
| Day-4 | |
| High vacuum applied and heating started | |
| Bath 110° C. | 1 hour |
| Bath 120° C. | 1 hour |

-continued

| | |
|---|---|
| Bath 130° C. | 1 hour |
| Bath 140° C. | 1 hour |
| Heating cut off allowed to room temperature, removed vacuum and kept under nitrogen | |
| Day-5 | |
| High vacuum applied and heating started | |
| Bath 160° C. | 7 hours |
| Heating cut off allowed to room temperature, removed vacuum, sealed the round bottom flask under nitrogen. | |

Batch-II

| Raw material | mw | Quantity | mmoles |
|---|---|---|---|
| Example 1 | 310 | 10 g | 32.25 |
| Ethylene glycol | 62.07 | 10 g | 161.10 |
| Dibutyl tin oxide | 248.92 | 1 mg | 0.004 |

In to a clean dry 100 mL 4 neck round bottomed flask equipped with nitrogen bubbler and distillation condenser were added terephthalic acid dimethoxy carbonyl methyl ester, ethylene glycol and dibutyl tin oxide under nitrogen atmosphere and heated as described below.

| Day-1 | |
|---|---|
| Bath 100° C. | 4 hours |
| Bath 120° C. | Over night |
| Day-2 | |
| Bath 120° C.-140° C. | 8 hours |
| Bath 140° C. | Over night |
| Day-3 | |
| Bath 150° C. | 1 hour |
| Bath 160° C. | 1 hour |
| Bath 170° C. | Over night |
| Day-4 | |
| Bath 180° C. | 2 hours |
| Bath 190° C. | 1 hour |
| Heating cut off allowed to room temperature | |
| Day-5 | |
| High vacuum applied and heating started | |
| Bath 120° C. | 8 hours |
| Heating cut off allowed to room temperature, removed vacuum and kept under nitrogen | |
| Day-6 | |
| High vacuum applied and heating started | |
| Bath 150° C. | 8 hours |
| Heating cut off allowed to room temperature, removed vacuum and kept under nitrogen | |
| Day-7 | |
| High vacuum applied and heating started | |
| Bath 160° C. | 9 hours |
| Heating cut off allowed to room temperature, removed vacuum and sealed the round bottom flask under nitrogen. | |

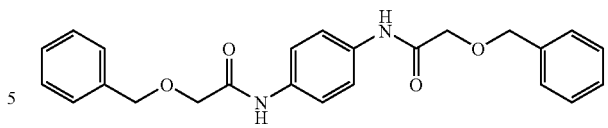

EXAMPLE 3

2-Benzyloxy-N-[4-(2-benzyloxy-acetylamino)-phenyl]-acetamide

To a mixture of 1,4-phenylenediamine (10 grams, 92.47 mmol), sodium bicarbonate (15.46 grams, 184.07 mmol) in ethyl acetate (100 mL) at 0° C. is added benzyloxy acetyl chloride (23.19 grams, 125.71 mmol) drop wise. The reaction mixture is stirred at room temperature for 10 hours. The solids are filtered, and the ethyl acetate layer is washed with 5% sodium bicarbonate solution (2×25 mL), water (2×25 mL), dried over sodium sulfate, and distilled to get crude 3, which can be purified by suitable solvent.

EXAMPLE 4

2-Hydroxy-N-[4-(2-hydroxy-acetylamino)-phenyl]-acetamide

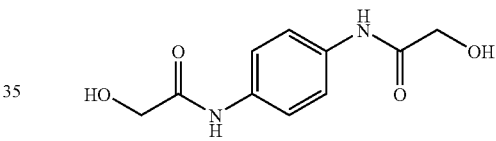

2-Benzyloxy-N-[4-(2-benzyloxy-acetylamino)-phenyl]-acetamide 3 (10 grams, 24.75 mmol) is dissolved in methanol (100 mL) in a pressure vessel. Pd/C (10%, 3 grams) is added, and the mixture is stirred under an atmosphere of hydrogen (4 Kg) for 5 hours. The catalyst is removed by filtration, and the methanol is distilled off. The crude 4 can be purified in a suitable solvent.

EXAMPLE 5

4-Nitro-benzoic acid methoxycarbonylmethyl ester

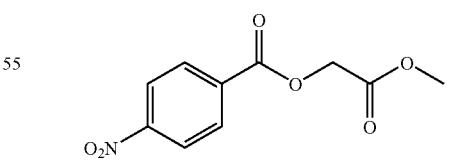

To mixture of 4-nitro benzoic acid (30 grams, 180 mmol) and triethylamine (45.5 grams, 450 mmol) in acetone (300 mL) was added methyl chloro acetate (29 grams, 267 mmol) drop wise, which was stirred under reflux for 20 hours. The solids were filtered off and the acetone distilled to give crude 5. Crude 5 was purified by column chromatography on silica gel using benzene as eluant to get pure 5 (16 grams, 37.3%) as a light yellow powder. M.p: 69-70.5° C. $^1$H NMR (CDCl$_3$) δ 3.80 (s,3H,ester), 4.86 (s,2H,CH$_2$), 8.26 (dd,4H,Ar).

EXAMPLE 6

4-Amino-benzoic acid methoxycarbonylmethyl ester

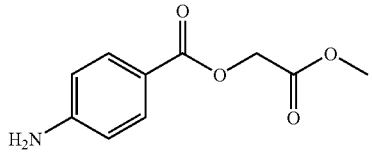

4-Nitro-benzoic acid methoxycarbonylmethyl ester 5 (15 grams, 62.76 mmol) was dissolved in methanol (150 mL) in a pressure vessel. Raney nickel (10 grams) was added, and the mixture stirred under an atmosphere of hydrogen (4 Kg) for 5 hours. The catalyst was removed by filtration and the methanol distilled off. The crude 6 was purified by column chromatography on silica gel using chloroform as eluant to get pure 6 (3 grams, 22.9%) as a white powder. M.p: 116-118° C. $^1$H NMR (CDCl$_3$) δ 3.78 (s,3H,ester), 4.15 (bs,2H,NH$_2$), 4.80 (s,2H,CH$_2$), 6.60 (d,2H,Ar), 7.90 (d,2H,Ar).

EXAMPLE 7

4-(2-Benzyloxy-acetylamino)-benzoic acid methoxycarbonylmethyl ester

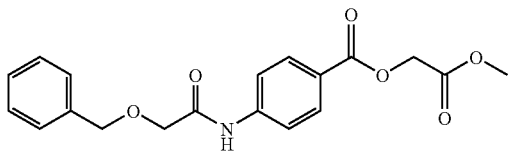

To a mixture of 4-amino-benzoic acid methoxycarbonylmethyl ester 6 (10 grams, 47.84 mmol) and sodium bicarbonate (8 grams, 95.23 mmol) in ethyl acetate (50 mL) at 0° C. is added benzyloxy acetyl chloride (12 grams, 65.04 mmol) drop wise. The reaction mixture is stirred at room temperature for 10 hours. The solids are filtered off, and the ethyl acetate layer is washed with 5% sodium bicarbonate solution (2×25 mL), water (2×25 mL), dried over sodium sulfate, and distilled to give crude 7, which can be purified via crystallized with a suitable solvent.

EXAMPLE 8

4-(2-Hydroxy-acetylamino)-benzoic acid methoxycarbonylmethyl ester

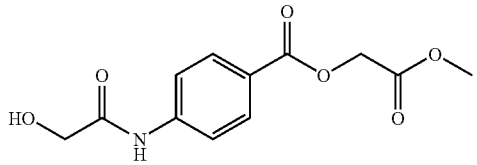

4-(2-Benzyloxy-acetylamino)-benzoic acid methoxycarbonylmethyl ester 7 (10 grams, 28.98 mmol) is dissolved in methanol (100 mL) in a pressure vessel. Pd/C (10%, 3 grams) is added, and the mixture is stirred under an atmosphere of hydrogen (4 Kg) for 5 hours. The catalyst is removed by filtration, and the methanol is distilled off. The crude 8 can be purified in a suitable solvent.

EXAMPLE 9

4-Isocyanato-benzoic acid methoxycarbonylmethyl ester

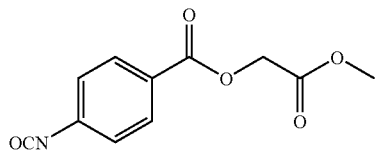

To a mixture of 4-amino-benzoic acid methoxycarbonylmethyl ester 6 (10 grams, 47.84 mmol) and triethylamine (9.68 grams, 95.67 mmol) in toluene (150 mL) under nitrogen atmosphere at 0° C. is added triphosgene (5.195 grams, 17.50 mmol) in one lot. Later the reaction mixture is heated to 75° C. over a period of one hour and maintained at this temperature for 20 hours. The reaction mixture is cooled to room temperature. The solids are filtered off, and the toluene is distilled under vacuum to give crude 11, which can be purified by a suitable method.

EXAMPLE 10

4-(2-Hydroxy-ethoxycarbonylamino)-benzoic acid methoxycarbonylmethyl ester

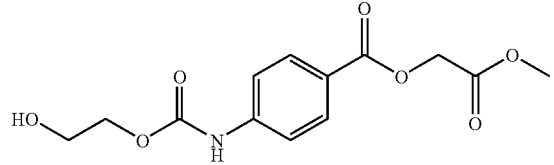

4-Isocyanato-benzoic acid methoxycarbonylmethyl ester 9 (5 grams, 21.09 mmol) is added to ethylene glycol (20 mL) at room temperature and stirred for 6 hours. Water (100 mL) is added, and crude 10 is filtered, dried, and purified by a suitable method.

EXAMPLE 11

4-Amino-benzoic acid methyl ester

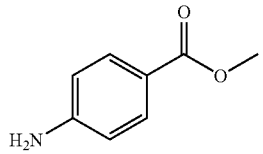

To a solution of 4-amino benzoic acid (100 grams, 729.18 mmol) in methanol (1000 mL) at 0° C. is passed dry HCl for 3 hours. The solution is then refluxed for 10 hours. Excess methanol is distilled, and water (1000 mL) is added. The

EXAMPLE 12

4-(2-Benzyloxy-acetylamino)-benzoic acid methyl ester

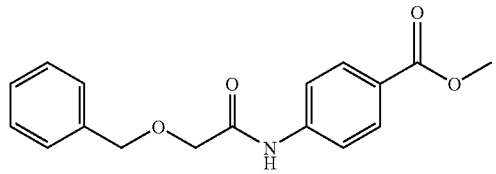

To a mixture of 4-amino-benzoic acid methyl ester 11 (10 grams, 66.15 mmol) and sodium bicarbonate (11 grams, 131.67 mmol) in ethyl acetate (150 mL) at 0° C. is added benzyloxy acetyl chloride (16.6 grams, 89.93 mmol) drop wise. The reaction mixture is stirred at room temperature for 10 hours. The solids are filtered off. The ethyl acetate layer is washed with 5% sodium bicarbonate solution (2×25 mL), water (2×25 mL), dried over sodium sulfate, and distilled to get crude 12, which can be purified in a suitable solvent.

EXAMPLE 13

4-(2-Hydroxy-acetylamino)-benzoic acid methyl ester

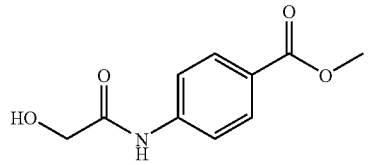

4-(2-benzyloxy-acetylamino)-benzoic acid methyl ester 12 (10 grams, 33.44 mmol) is dissolved in methanol (100 mL) in a pressure vessel. Pd/C (10%, 3 grams) is added, and the mixture is stirred under an atmosphere of hydrogen (4 Kg) for 5 hours. The catalyst is removed by filtration and the methanol distilled off. The crude 13 can be purified in a suitable solvent.

In Vitro Hydrolysis of Functionalized Aromatics

A compound and a polymer of the present invention were examined for their rates of hydrolysis as described below.

EXAMPLE 14

4-Methoxycarbonylmethoxycarbonylmethoxy-benzoic acid methoxycarbonyl methyl ester

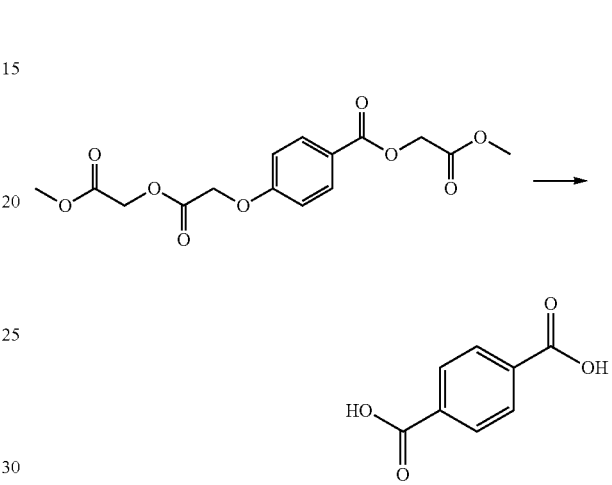

| Compound | 100 mg |
| --- | --- |
| Aldrich pH 7.4 buffer | 10 mL |
| Temperature | 100° C. |
| Method | Monitoring by TLC for disappearance of starting material |
| Hydrolyzed in 26.5 hours | |
| Compound | 100 mg |
| Aldrich pH 9 buffer | 10 mL |
| Dilution | 1% solution |
| Temperature | 100° C. |
| Method | Monitoring by TLC for disappearance of starting material |
| Hydrolyzed in 5 hours | |

EXAMPLE 15

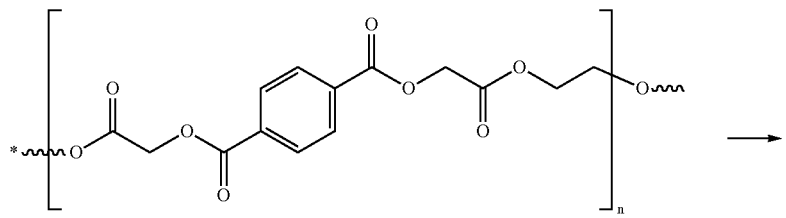

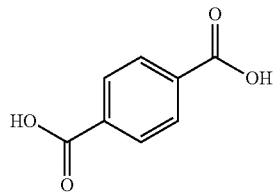

| | |
|---|---|
| Polymer | 100 mg |
| Aldrich pH 7.4 buffer: | 10 mL |
| Temperature | 100° C. |
| Method | Monitoring by TLC for disappearance of starting material |
| Hydrolyzed in 50-60% in 118 hours | |
| Polymer | 100 mg |
| Aldrich pH 4 buffer | 10 mL |
| Temperature | 100° C. |
| Method | Monitoring by TLC for disappearance of starting material |
| Hydrolyzed in 50% in 17 hours | |
| Polymer | 100 mg |
| Aldrich pH 9 buffer | 10 mL |
| Temperature | 100° C. |
| Method | Monitoring by TLC for disappearance of starting material |
| Hydrolyzed in 70% in 13 hours | |

The above hydrolysis examples indicate that the difunctionalized aromatic compounds of the present invention hydrolyze and also that polymers derived from the difunctionalized aromatic compounds hydrolyze. Therefore, using the difunctionalized aromatic compounds, it is expect that one can develop polymers with controlled hydrolysis profiles.

What is claimed is:

1. A polymer, comprising: a first repeating unit, which is a difunctionalized aromatic of formula I:

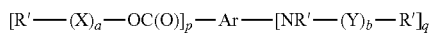

and a second repeating unit formed from a compound selected from a dicarboxylic acid, a dialcohol, a diisocyanate, an amino-alcohol, a hydroxycarboxylic acid, and a diamine; wherein:
Ar is an aromatic ring substituted with 1, 2, or 3 R groups;
X is independently at each occurrence selected from: —$CH_2COO$—; —$CH(CH_3)COO$—; —$CH_2CH_2OCH_2COO$—; —$CH_2CH_2CH_2CH_2CH_2COO$—; —$(CH_2)_yCOO$—; and, —$(CH_2CH_2O)_zCH_2COO$—, where y is independently selected from 2, 3, 4 and 6-24 and z is independently selected from 2-24;
Y is independently at each occurrence selected from: —$COCH_2O$—; —$COCH(CH_3)O$—; —$COCH_2OCH_2CH_2O$—; —$COCH_2CH_2CH_2CH_2CH_2O$—; —$CO(CH_2)_mO$—; and, —$COCH_2$—O—$(CH_2CH_2O)_n$—, where m is selected from 2-4 and 6-24 and n is selected from 2-24;
R' is selected from hydrogen, benzyl, and $C_{1-6}$ alkyl;
p and q are independently selected from 0, 1, 2, 3, and 4, provided that p+q total 2, 3, or 4;
a and b are independently selected from 0, 1, 2, 3, and 4, provided that a+b total from 1, 2, 3, 4, 5, or 6;
R is independently selected from —O—$(X)_c$—R' and —O—$(Y)_c$—R';
c is independently selected from 0, 1, 2, 3, and 4;
alternatively, R is independently selected from H, =O, O-glycosides, —$(CH_2)_{0-2}$—$OR^a$, —$(CH_2)_{0-2}$—$C_6H_5$, —$(CH_2)_{0-2}$—CHO, Cl, F, Br, I, —$(CH_2)_{0-2}$—OC(O)—$R^a$, —$(CH_2)_{0-2}$—$CO_2$—$R^a$, —$(C(CH_3))_{0-2}$—$CO_2$—$R^a$, —$(CH_2)_{1-2}CO_2$—$(CH_2)_{1-2}$—$CO_2$—$R^a$, —$(C(CH_3))_{1-2}$—$CO_2$—$(CH_2)_{1-2}$—$CO_2$—$R^a$, —$(CH_2)_{0-2}$—CO—$R^a$, —$O(CH_2)_{0-2}$—$C_6H_5$, —$O(CH_2)_{1-2}$—$CO_2$—$R^a$, —$O(C(CH_3))_{1-2}$—$CO_2$—$R^a$, —$O(CH_2)_{1-2}$—CO—$R^a$, —$(CH_2)_{0-2}$—$NO_2$, —$(CH_2)_{0-2}NR^aR^a$, —$(CH_2)_{0-2}$—$NR^aCOR^a$, —$(CH_2)_{1-2}$—$NR^aC(O)(CH_2)_{1-2}OR^a$, —$C_6H_5$, —$C_6H_5OR^a$, and —$C_6H_5$—CH=$CHCO_2R^a$; and,
$R^a$ is independently selected from H and $C_{1-6}$ alkyl.

2. The polymer of claim 1, wherein
X is independently at each occurrence selected from:
—$CH_2COO$—;
—$CH(CH_3)COO$—;
—$CH_2CH_2OCH_2COO$—; and,
—$CH_2CH_2CH_2CH_2CH_2COO$—;
Y is independently at each occurrence selected from:
—$COCH_2O$—; —$COCH(CH_3)O$—;
—$COCH_2OCH_2CH_2O$—;
—$COCH_2CH_2CH_2CH_2CH_2O$—;
p and q are independently selected from 0, 1, 2, and 3, provided that p+q total 1, 2, or 3;
a and b are independently selected from 0, 1, 2, and 3, provided that a+b total from 1, 2, 3, or 4; and,
c is independently selected from 0, 1, 2, and 3.

3. The polymer of claim 1, wherein:
X is independently at each occurrence selected from: —$CH_2COO$— and —$CH(CH_3)COO$—;
Y is independently at each occurrence selected from: —$COCH_2O$— and —$COCH(CH_3)O$—;
a and b are independently selected from 0, 1, and 2, provided that a+b total from 1, 2, 3, or 4; and,
c is independently selected from 0, 1, and 2.

4. The polymer of claim 1, wherein the difunctionalized aromatic is of formula Ia-Ic:

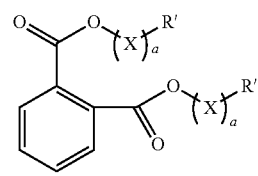

Ia

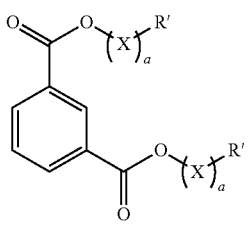

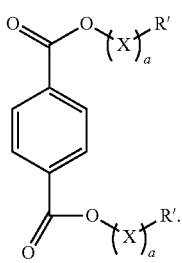

5. The polymer of claim 1, wherein the difunctionalized aromatic is of formula IIa-IIc:

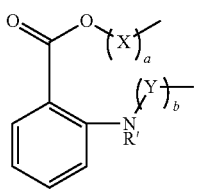

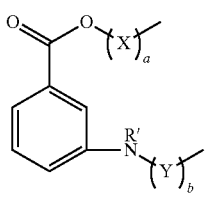

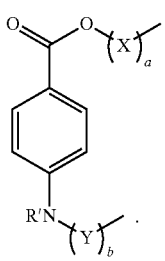

6. The polymer of claim 1, wherein the difunctionalized aromatic is of formula IIIa-IIIc:

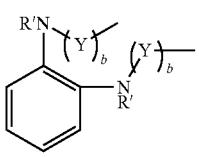

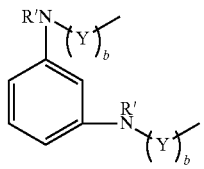

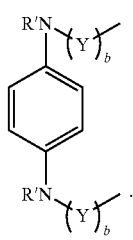

7. The polymer of claim 1, wherein the polymer, further comprises: a second functionalized aromatic.

8. The polymer of claim 1, wherein the polymer is further polymerized with a lactone monomer.

9. The polymer of claim 8, wherein the lactone monomer is selected from glycolide, lactide, ε-caprolactone, trimethylene carbonate, and p-dioxanone.

10. An implantable medical device, comprising: a polymer of claim 1.

11. The implantable medical device of claim 10, wherein the polymer has been further polymerized with a lactone monomer selected from glycolide, lactide, ε-caprolactone, trimethylene carbonate, and p-dioxanone.

12. The implantable medical device of claim 10, wherein the device is a stent.

13. The implantable medical device of claim 12, wherein the polymer has been further polymerized with a lactone monomer selected from glycolide, lactide, ε-caprolactone, trimethylene carbonate, and p-dioxanone.

14. The implantable medical device of claim 10, wherein the device is a scaffold for tissue engineering, comprising: a porous structure for the attachment and proliferation of cells.

15. The implantable medical device of claim 14, wherein the polymer has been further polymerized with a lactone monomer selected from glycolide, lactide, ε-caprolactone, trimethylene carbonate, and p-dioxanone.

16. A coating for a stent, comprising: a polymer of claim 1.

17. The stent coating of claim 16, wherein the polymer has been further polymerized with a lactone monomer selected from glycolide, lactide, ε-caprolactone, trimethylene carbonate, and p-dioxanone.

18. A drug delivery system, comprising: a polymer of claim 1 physically admixed with a biologically or pharmacologically active agent.

19. The drug delivery system of claim 18, wherein the biologically or pharmacologically active agent is physically embedded or dispersed into the polymer and the polymer is in the form of a polymeric matrix.

20. The drug delivery system of claim 18, wherein the polymer has been further polymerized with a lactone monomer selected from glycolide, lactide, ε-caprolactone, trimethylene carbonate, and p-dioxanone.

21. A polymer blend, comprising: two different polymers of claim 1.

22. A cosmetic composition, comprising at least one polymer of claim 1 and a cosmetic ingredient.

23. A polymer of claim 1, wherein the polymer has been sterilized by cobalt-60 radiation, electron beam radiation, and/or ethylene oxide.

24. The polymer of claim 23, wherein the polymer has been sterilized by cobalt-60 radiation.

25. The polymer of claim 1, wherein the difunctionalized aromatic repeating unit was formed from a difunctionalized aromatic compound, comprising: at least two active sites for polymerization, selected from: two hydroxyl groups, a hydroxyl group and a carboxylic acid, a hydroxyl group and an amine group, a carboxylic acid group and an amino group; and two carboxylic acid groups.

26. The polymer of claim 25, wherein the at least two active sites for polymerization, are two hydroxyl groups.

27. The polymer of claim 25, wherein the at least two active sites for polymerization, are a hydroxyl group and a carboxylic acid.

28. The polymer of claim 25, wherein the at least two active sites for polymerization, are a hydroxyl group and an amine group.

29. The polymer of claim 25, wherein the at least two active sites for polymerization, are a carboxylic acid group and an amino group.

30. The polymer of claim 25, wherein the at least two active sites for polymerization, are two carboxylic acid groups.

31. The polymer of claim 1, wherein the second repeating unit is formed from a compound selected from a dicarboxylic acid.

32. The polymer of claim 1, wherein the second repeating unit is formed from a compound selected from a dialcohol.

33. The polymer of claim 1, wherein the second repeating unit is formed from a compound selected from a diisocyanate.

34. The polymer of claim 1, wherein the second repeating unit is formed from a compound selected from an amino-alcohol.

35. The polymer of claim 1, wherein the second repeating unit is formed from a compound selected from a hydroxycarboxylic acid.

36. The polymer of claim 1, wherein the second repeating unit is formed from a compound selected from a diamine.

37. The polymer of claim 1, wherein Ar is selected from phenyl, bi-phenyl, and naphthyl and is substituted with 1, 2, or 3 R.

38. The polymer of claim 37, wherein Ar is phenyl and is substituted with 1, 2, or 3 R.

39. The polymer of claim 37, wherein Ar is bi-phenyl and is substituted with 1, 2, or 3 R.

40. The polymer of claim 37, wherein Ar is naphthyl and is substituted with 1, 2, or 3 R.

41. The polymer of claim 2, wherein Ar is selected from phenyl, bi-phenyl, and naphthyl and is substituted with 1, 2, or 3 R.

42. The polymer of claim 41, wherein Ar is phenyl and is substituted with 1, 2, or 3 R.

43. The polymer of claim 41, wherein Ar is bi-phenyl and is substituted with 1, 2, or 3 R.

44. The polymer of claim 41, wherein Ar is naphthyl and is substituted with 1, 2, or 3 R.

45. The polymer of claim 3, wherein Ar is selected from phenyl, bi-phenyl, and naphthyl and is substituted with 1, 2, or 3 R.

46. The polymer of claim 45, wherein Ar is phenyl and is substituted with 1, 2, or 3 R.

47. The polymer of claim 45, wherein Ar is bi-phenyl and is substituted with 1, 2, or 3 R.

48. The polymer of claim 45, wherein Ar is naphthyl and is substituted with 1, 2, or 3 R.

49. A medical device, comprising: a polymer of claim 1, wherein the device is selected from: molded articles, surgical clips, staples, sutures, coatings, fibers, filaments, rods, films, and knitted products.

50. The medical device of claim 49, wherein the molded article is selected from vascular grafts, stents, bone plates, sutures, implantable sensors, and barriers for surgical adhesion prevention.

51. The medical device of claim 49, wherein the coating is selected from an endoscopic instrument coating, a suture coating, a stent coating, and a needle coating.

52. The medical device of claim 49, wherein the fibers or filaments are suitable for fabrication into sutures, ligatures, multifilament yarn, sponges, gauze, tubes, and sheets for typing up and supporting damaged surface abrasions.

53. The medical device of claim 49, wherein the polymer has been further polymerized with a lactone monomer selected from glycolide, lactide, ϵ-caprolactone, trimethylene carbonate, and p-dioxanone.

* * * * *

UNITED STATES PATENT AND TRADEMARK OFFICE
CERTIFICATE OF CORRECTION

PATENT NO. : 8,007,526 B2  Page 1 of 1
APPLICATION NO. : 11/565820
DATED : August 30, 2011
INVENTOR(S) : Rao S. Bezwada It is certified that error appears in the above-identified patent and that said Letters Patent is hereby corrected as shown below:

Column 33, line 41, in formula I, both occurrences of "R'" should be deleted.

Column 34, lines 60-65, in formula Ia, both occurrences of "R'" should be replaced by "]".

Column 35, lines 1-20, in formula Ib and formula Ic, all four occurrences of "R'" should be replaced by "]".

Signed and Sealed this
Fourth Day of October, 2011

David J. Kappos
*Director of the United States Patent and Trademark Office*